(12) United States Patent
Hultgren et al.

(10) Patent No.: US 9,017,071 B2
(45) Date of Patent: Apr. 28, 2015

(54) DENTAL OCCLUSION ANALYSIS TOOL

(71) Applicants: Bruce W. Hultgren, Victoria, MN (US);
Robert Isaacson, Edina, MN (US);
Michael C. Marshall, Sheboygan, WI
(US)

(72) Inventors: Bruce W. Hultgren, Victoria, MN (US);
Robert Isaacson, Edina, MN (US);
Michael C. Marshall, Sheboygan, WI
(US)

(73) Assignee: Bruce W. Hultgren, Victoria, MN (US)

( * ) Notice: Subject to any disclaimer, the term of this patent is extended or adjusted under 35 U.S.C. 154(b) by 0 days.

(21) Appl. No.: 14/084,187

(22) Filed: Nov. 19, 2013

(65) Prior Publication Data
US 2014/0205964 A1 Jul. 24, 2014

Related U.S. Application Data

(63) Continuation of application No. 13/020,573, filed on Feb. 3, 2011, now Pat. No. 8,585,400.

(60) Provisional application No. 61/301,136, filed on Feb. 3, 2010.

(51) Int. Cl.
A61C 1/00 (2006.01)
A61C 7/00 (2006.01)
A61C 19/04 (2006.01)

(52) U.S. Cl.
CPC . A61C 7/002 (2013.01); A61C 7/00 (2013.01); A61C 19/04 (2013.01)

(58) Field of Classification Search
USPC .............................. 433/2, 24, 68, 229
See application file for complete search history.

(56) References Cited

U.S. PATENT DOCUMENTS

| | | |
|---|---|---|
| 5,882,192 A | 3/1999 | Bergersen |
| 6,217,334 B1 | 4/2001 | Hultgren |
| 6,250,918 B1 | 6/2001 | Sachdeva et al. |
| 6,413,083 B1 | 7/2002 | Hamilton |
| 6,579,059 B2 | 6/2003 | Chen |
| 6,602,070 B2 | 8/2003 | Miller et al. |
| 6,632,089 B2 | 10/2003 | Rubbert et al. |
| 7,029,275 B2 | 4/2006 | Rubbert et al. |
| 7,080,979 B2 | 7/2006 | Rubbert et al. |
| 7,210,929 B2 | 5/2007 | Raby et al |

(Continued)

FOREIGN PATENT DOCUMENTS

| | | |
|---|---|---|
| EP | 2 020 951 A0 | 2/2009 |
| WO | WO 94/10935 | 5/1994 |

(Continued)

OTHER PUBLICATIONS

U.S. Appl. No. 11/800,430, filed May 2007, Hultgren et al.

(Continued)

Primary Examiner — Edward Moran
(74) Attorney, Agent, or Firm — Merchant & Gould P.C.

(57) ABSTRACT

An electronic 3D model of at least a portion of a maxillary arch of a patient is displayed. Inputs indicating a peak of a mesiobuccal cusp of a maxillary first molar are received for both the patient's right and left sides. In addition, an electronic 3D model of at least a portion of a mandibular arch of a patient is displayed. Inputs indicating relevant points on the mandibular first molar are received for both the patient's right and left sides. Side scores are generated for the patient's right and left sides based on the indicated points. A final occlusion score for the patient is displayed. The final occlusion score is based on the side score for the right side and the side score for the left side.

9 Claims, 15 Drawing Sheets

(56) References Cited

U.S. PATENT DOCUMENTS

| | | |
|---|---|---|
| 7,744,369 B2 | 6/2010 | Imgrund et al. |
| 8,108,189 B2 | 1/2012 | Chelnokov et al. |
| 8,401,826 B2 | 3/2013 | Cheng et al. |
| 8,585,400 B2 * | 11/2013 | Hultgren et al. ............ 433/24 |
| 2002/0025503 A1 | 2/2002 | Chapoulaud et al. |
| 2002/0031742 A1 | 3/2002 | Hamilton |
| 2004/0029068 A1 | 2/2004 | Sachdeva et al. |
| 2004/0038168 A1 | 2/2004 | Choi et al. |
| 2004/0259049 A1 | 12/2004 | Kopelman et al. |
| 2006/0263739 A1 | 11/2006 | Sporbert et al. |
| 2006/0263741 A1 | 11/2006 | Imgrund et al. |
| 2007/0154866 A1 | 7/2007 | Hall |
| 2008/0057462 A1 | 3/2008 | Kitching et al. |
| 2008/0286712 A1 | 11/2008 | Imgrund et al. |
| 2009/0061382 A1 | 3/2009 | Wen |
| 2009/0098502 A1 | 4/2009 | Andreiko |
| 2009/0286712 A1 | 11/2009 | Gallotti |
| 2010/0145664 A1 | 6/2010 | Hultgren et al. |
| 2010/0169057 A1 | 7/2010 | Hultgren et al. |
| 2011/0189625 A1 | 8/2011 | Hultgren |
| 2011/0191075 A1 | 8/2011 | Hultgren |
| 2011/0244415 A1 | 10/2011 | Batesole |

FOREIGN PATENT DOCUMENTS

| | | |
|---|---|---|
| WO | WO 03/094102 A1 | 11/2003 |
| WO | WO 2007/130573 A2 | 11/2007 |
| WO | WO 2007/130574 A1 | 11/2007 |

OTHER PUBLICATIONS

U.S. Appl. No. 11/999,891, filed Dec. 2007, Isaacson et al.
U.S. Appl. No. 12/169,567, filed Jul. 2008, Isaacson et al.
U.S. Appl. No. 12/359,993, filed Jan. 2009, Isaacson et al.
U.S. Appl. No. 12/299,581, filed Nov. 2008, Hultgren.
U.S. Appl. No. 11/999,892, filed Dec. 2007, Isaacson et al.
U.S. Appl. No. 11/800,449, filed May 2007, Isaacson et al.
U.S. Appl. No. 13/383,408, filed Jan. 2012, Isaacson et al.
U.S. Appl. No. 13/623,754, filed Sep. 2012, Isaacson et al.
Vardimon, A. et al., "Cortical bone remodeling/tooth movement ratio during maxillary incisor retraction with tip versus torque movements," *Am. J. Orthod. Dentofacial Orthop.*, vol. 114, No. 5, pp. 520-529 (Nov. 1998).
George Papaioannou, NPL Publication, "Joints, Biomechanis of", 63 pages, (Feb. 2006).
Jan Edwards, "Rotation and Translation of the Jaw During Speech", 16 pages, (1990).
Kazuo Hayashi, "Simulation Study for a Finite Helical Axis Analysis of Tooth Movement" 6 pages, (2005).
International Search Report in PCT/US2007/010839 mailed Oct. 17, 2007.
International Search Report in PCT/US2007/010838 mailed Jul. 11, 2007.

* cited by examiner

DENTAL OCCLUSION ANALYSIS TOOL

This application is a continuation of U.S. Pat. No. 8,585,400, issued Nov. 19, 2013, entitled DENTAL OCCLUSION ANALYSIS TOOL, which claims the benefit of U.S. Provisional Application Serial No. 61/301,136, filed Feb. 3, 2010, entitled DENTAL OCCLUSION ANALYSIS TOOL, the disclosures of which are incorporated by reference herein in their entireties. To the extent appropriate, a claim of priority is made to each of the above disclosed applications.

BACKGROUND

The American Board of Orthodontics (ABO) certifies orthodontists as board certified orthodontists. To be certified, an orthodontist must submit sets of before and after models of work performed by the orthodontist. A before model is a model of a patient's dentition before the orthodontist treated the patient and an after model is a model of the patient's dentition after the orthodontist treated the patient. The ABO uses the before and after models to determine whether the orthodontist successfully treated the patient. If the ABO determines that the orthodontist successfully treated the patient, the orthodontist is eligible to be certified.

The ABO requires that the cases submitted by an orthodontist must be sufficiently difficult to treat. In other words, the ABO does not want to certify an orthodontist who can only show that she or he can successfully treat easy cases. Accordingly, the ABO has developed a test for analyzing the difficulty of treating a case. The test involves analysis of several characteristics of a patient's dentition. These characteristics include overjet, overbite, openbite, crowding, occlusion, crossbite, and other patient characteristics. Currently, the ABO performs the test by physically measuring physical plaster models of a patient's dentition.

However, there are drawbacks associated with physically measuring physical plaster models. For example, physically measuring physical plaster models can be a time consuming process. Furthermore, physically measuring physical plaster models can introduce a certain amount of subjectivity to the measurements. Accordingly, there is a need in the art for methods and systems for performing the test that overcome the drawbacks of the prior art.

SUMMARY

Electronic three-dimensional (3D) models are created by scanning the before and after models submitted by an orthodontist to the ABO. In some embodiments, such electronic 3D models are created by scanning the dentition of patients in accordance with U.S. Pat. No. 6,217,334, the entire content of which is hereby incorporated by reference. However, in other embodiments, other techniques are used to create the electronic 3D models.

An electronic 3D model of at least a portion of a maxillary arch of a patient is displayed. Inputs indicating a peak of a mesiobuccal cusp of a maxillary first molar are received for both the patient's right and left sides. In addition, an electronic 3D model of at least a portion of a mandibular arch of a patient is displayed. Inputs indicating relevant points on the mandibular first molar are received for both the patient's right and left sides. Side scores are generated for the patient's right and left sides based on the indicated points. A final occlusion score for the patient is displayed. The final occlusion score is based on the side score for the right side and the side score for the left side.

One aspect is a computer-implemented method for analyzing occlusion. The computer-implemented method comprises for both a right side of a patient and a left side of the patient: displaying an electronic 3D model of at least a portion of a maxillary arch of the patient. In addition, the method comprises method comprises for both a right side of a patient and a left side of the patient receiving input indicating a first point on the electronic 3D model of the portion of the maxillary arch. The first point corresponds to a peak of a mesiobuccal cusp of a maxillary first molar. Furthermore, the method comprises for both a right side of a patient and a left side of the patient displaying an electronic 3D model of at least a portion of a mandibular arch of the patient. In addition, the method comprises for both a right side of a patient and a left side of the patient receiving input indicating a second point on the electronic 3D model of the portion of the mandibular arch. The second point corresponds to a peak of a mesiobuccal cusp of a mandibular first molar. Furthermore, the method comprises for both a right side of a patient and a left side of the patient receiving input indicating a third point on the electronic 3D model of the portion of the mandibular arch. The third point corresponds to a peak of a distobuccal cusp of the mandibular first molar. In addition, the method comprises for both a right side of a patient and a left side of the patient receiving input indicating a fourth point on the electronic 3D model of the portion of the mandibular arch. The fourth point corresponds to a contact point between the mandibular first molar and a mandibular second premolar. Moreover, the method comprises for both a right side of a patient and a left side of the patient receiving input indicating a fifth point on the electronic 3D model of the portion of the mandibular arch. The fifth point corresponds to a contact point between the mandibular first molar and a mandibular second molar. In addition, the method comprises for both a right side of a patient and a left side of the patient generating, by a computing device, a central axis. The central axis is a line on a plane. The plane is parallel to an occlusal plane of the patient. Furthermore, the method comprises for both a right side of a patient and a left side of the patient identifying a location of a scoring intersection. The scoring intersection is a point where the central axis and a scoring line intersect. The scoring line is a line on the plane. The scoring line is perpendicular to the central axis and passes through a point projected onto the plane by the first point. In addition, the method comprises for both a right side of a patient and a left side of the patient generating a side score based on the location of the scoring intersection relative to measurement intersections. The measurement intersections are points where the central axis and measurement lines intersect. The measurement lines include lines on the plane perpendicular to the central axis. In addition, the method comprises displaying a final occlusion score for the patient, the final occlusion score based on the side score for the right side and the side score for the left side.

In another aspect, a computing device comprises a processing unit and a set of computer-readable data storage media comprising at least one computer-readable data storage medium. The set of computer-readable data storage media stores software instructions that, when executed by the processing unit, cause the computing device to, for both a right side of a patient and a left side of the patient, display an electronic 3D model of at least a portion of a maxillary arch of the patient. In addition, the software instructions cause the computing device to, for both a right side of a patient and a left side of the patient, receive input indicating a first point on the electronic 3D model of the portion of the maxillary arch. The first point corresponds to a peak of a mesiobuccal cusp of a maxillary first molar. Furthermore, the software instructions cause the computing device to, for both a right side of a patient and a left side of the patient, display an electronic 3D model of at least a portion of a mandibular arch of the patient. In addition, the software instructions cause the computing device to, for both a right side of a patient and a left side of the patient, receive input indicating a second point on the electronic 3D model of the portion of the mandibular arch. The second point corresponds to a peak of a mesiobuccal cusp of a mandibular first molar. Furthermore, the software instructions cause the computing device to, for both a right side of a patient and a left side of the patient, receive input indicating a third point on the electronic 3D model of the portion of the mandibular arch. The third point corresponds to a peak of a distobuccal cusp of the mandibular first molar. In addition, the software instructions cause the computing device to, for both a right side of a patient and a left side of the patient, receive input indicating a fourth point on the electronic 3D model of the portion of the mandibular arch. The fourth point corresponds to a contact point between the mandibular first molar and a mandibular second premolar. Furthermore, the software instructions cause the computing device to, for both a right side of a patient and a left side of the patient, receive input indicating a fifth point on the electronic 3D model of the portion of the mandibular arch. The fifth point corresponds to a contact point between the mandibular first molar and a mandibular second molar. In addition, the software instructions cause the computing device to, for both a right side of a patient and a left side of the patient, generate a central axis. The central axis being a line on a plane. The plane is parallel to an occlusal plane of the patient. Furthermore, the software instructions cause the computing device to, for both a right side of a patient and a left side of the patient, identify a location of a scoring intersection. The scoring intersection is a point where the central axis and a scoring line intersect. The scoring line is a line on the plane. The scoring line is perpendicular to the central axis and passes through a point projected onto the plane by the first point. In addition, the software instructions cause the computing device to, for both a right side of a patient and a left side of the patient, generate a side score based on the location of the scoring intersection relative to measurement intersections. The measurement intersections are points where the central axis and measurement lines intersect. The measurement lines include lines on the plane perpendicular to the central axis. The software instructions also cause the computing device to display a final occlusion score for the patient. The final occlusion score is based on the side score for the right side and the side score for the left side.

In another aspect, a computer-readable data storage medium comprises software instructions that, when executed by a processing unit of a computing device, cause the computing device to, for both a right side of a patient and a left side of the patient, display an electronic 3D model of at least a portion of a maxillary arch of the patient. In addition, the software instructions cause the computing device to, for both a right side of a patient and a left side of the patient, receive input indicating a first point on the electronic 3D model of the portion of the maxillary arch. The first point corresponds to a peak of a mesiobuccal cusp of a first maxillary molar. Furthermore, the software instructions cause the computing device to, for both a right side of a patient and a left side of the patient, display an electronic 3D model of at least a portion of a mandibular arch of the patient. In addition, the software instructions cause the computing device to, for both a right side of a patient and a left side of the patient, receive input indicating a second point on the electronic 3D model of the portion of the mandibular arch. The second point corresponds to a peak of a mesiobuccal cusp of a first mandibular molar. Furthermore, the software instructions cause the computing device to, for both a right side of a patient and a left side of the patient, receive input indicating a third point on the electronic 3D model of the portion of the mandibular arch. The third point corresponds to a peak of a distobuccal cusp of the first mandibular molar. In addition, the software instructions cause the computing device to, for both a right side of a patient and a left side of the patient, receive input indicating a fourth point on the electronic 3D model of the portion of the mandibular arch. The fourth point corresponds to a contact point between the first mandibular molar and a second mandibular premolar. In addition, the software instructions cause the computing device to, for both a right side of a patient and a left side of the patient, receive input indicating a fifth point on the electronic 3D model of the portion of the mandibular arch. The fifth point corresponds to a contact point between the first mandibular molar and a second mandibular molar. Furthermore, the software instructions cause the computing device to, for both a right side of a patient and a left side of the patient, generate a central axis. The central axis is a line on a plane. The plane is parallel to an occlusal plane of the patient. In addition, the software instructions cause the computing device to, for both a right side of a patient and a left side of the patient, identify a location of a scoring intersection. The scoring intersection is a point where the central axis and a scoring line intersect. The scoring line is a line on the plane. The scoring line is perpendicular to the central axis and passing through a point projected onto the plane by the first point. Furthermore, the software instructions cause the computing device to, for both a right side of a patient and a left side of the patient, generate a side score based on the location of the scoring intersection relative to measurement intersections. The measurement intersections are points where the central axis and measurement lines intersect. The measurement lines include lines on the plane perpendicular to the central axis. In addition, the software instructions cause the computing device to display a final occlusion score for the patient. The final occlusion score is based on the side score for the right side and the side score for the left side.

Yet another aspect is a method for analyzing occlusion. The method comprises providing, to a computing device, input indicating a first point on an electronic 3D model of a portion of a maxillary arch of a patient. The first point corresponds to a peak of a mesiobuccal cusp of a first maxillary molar. The method also comprises providing, to the computing device, input indicating a second point on an electronic 3D model of the portion of a mandibular arch of the patient. The second point corresponds to a peak of a mesiobuccal cusp of a first mandibular molar. In addition, the method comprises providing, to the computing device, input indicating a third point on the electronic 3D model of the portion of the mandibular arch. The third point corresponds to a peak of a distobuccal cusp of the first mandibular molar. The method also comprises providing, to the computing device, input indicating a fourth point on the electronic 3D model of the portion of the mandibular arch. The fourth point corresponds to a contact point between the first mandibular molar and a second mandibular premolar. The method also comprises providing, to the computing device, input indicating a fifth point on the electronic 3D model of the portion of the mandibular arch. The fifth point corresponds to a contact point between the first mandibular molar and a second mandibular molar. In addition, the method comprises reviewing, by a user, a final occlusion score for the patient. The final occlusion score is based at least in part on a side score of the patient. The side score of the patient is based on a location of a scoring intersection relative to measurement intersections. The measurement intersections are points where a central axis and measurement lines intersect. The measurement lines and the central axis being lines on a plane. The plane is parallel to an occlusal plane of the patient. The measurement lines include lines that are perpendicular to the central axis. The scoring intersection is a point where the central axis and a scoring line intersect. The scoring line is a line on the plane perpendicular to the central axis and passing through the point projected onto the plane by the first point.

This summary is provided to introduce a selection of concepts in a form that are further described below in the Detailed Description. This Summary is not intended to identify key features or essential features of the claimed subject matter, nor is it intended to be used to limit the scope of the claimed subject matter.

DETAILED DESCRIPTION

Figure 1:
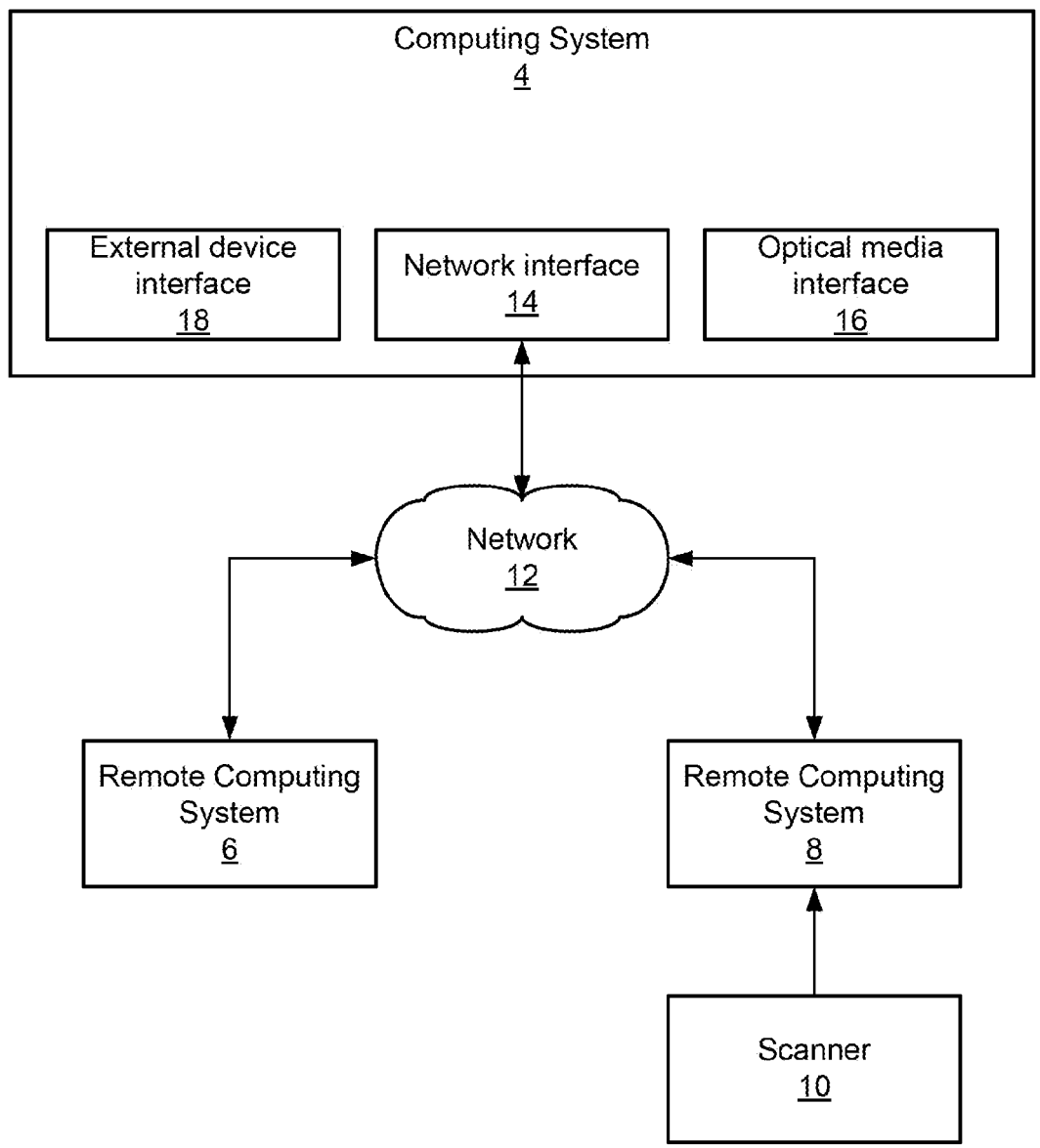
FIG. 1 is a block diagram illustrating an example system for evaluating the difficulty of treating an orthodontic case.

FIG. 1 is a block diagram illustrating an example system 2 for evaluating the difficulty of treating an orthodontic case. As illustrated in the example of FIG. 1, the system 2 includes a computing system 4, a remote computing system 6, a remote computing system 8, a scanner 10, and a network 12. It should be appreciated that the system 2 illustrated in the example of FIG. 1 is merely one embodiment. Other embodiments include more, fewer, or different components (e.g., computing systems, networks, devices, etc.) than those shown in the example of FIG. 1.

Each of the computing system 4, the remote computing system 6, and the remote computing system 8 is a system comprising one or more computing devices. A computing device is an electronic device that processes information. Example types of computing devices include desktop computers, laptop computers, netbooks, server computers, mainframe computers, supercomputers, handheld computers, video game consoles, smartphones, television set top boxes, computers integrated into vehicles, and other types of electronic devices that process information. Furthermore, in some embodiments, the computing system 4, the remote computing system 6, and the remote computing system 8 comprise computing devices of the type illustrated in the example of FIG. 15.

In embodiments where the computing system 4 comprises more than one computing device, the functionality of the computing system 4 is distributed among the computing devices included in the computing system 4. For example, one computing device in the computing system 4 may store and retrieve data while another computing device in the computing system 4 may process the data for viewing by users. Similarly, in embodiments where the remote computing system 6 or the remote computing system 8 comprise more than one computing device, the functionality of the remote computing system 6 or the remote computing system 8 is distributed among the computing devices included in the remote computing system 6 or the remote computing system 8.

The network 12 facilitates communication among the computing system 4, the remote computing system 6, and the remote computing system 8. The network 12 is a system of devices interconnected by wired or wireless links. In various embodiments, the network 12 is implemented in various ways. For example, in some embodiments, the network 12 is implemented as one or more wide area networks, such as the Internet. In other embodiments, the network 12 is implemented as one or more local area networks or networks on other scales.

The scanner 10 is a device that generates electronic 3D models of a patient's dentition. In various embodiments, the scanner 10 generates electronic 3D models in various ways. For example, in some embodiments, a plaster cast of a dental arch of a patient is positioned in the scanner 10. The scanner 10 takes measurements of the plaster cast and uses the measurements to generate an electronic 3D model of the patient's dental arch. In various embodiments, the scanner 10 takes the measurements in various ways. For example, in some embodiments, the scanner 10 uses a laser to take the measurements, such as described in U.S. Pat. No. 6,217,334. In other embodiments, the scanner 10 uses a tangible probe to take the measurements. Furthermore, in other embodiments, the scanner 10 is an intra-oral camera that captures electronic two-dimensional images of a patient's teeth and gums. In such embodiments, the electronic two-dimensional images are processed to generate electronic 3D models.

The scanner 10 provides the electronic 3D models to the remote computing system 8. A user of the remote computing system 8 is then able to use the remote computing system 8 to review the electronic 3D models. Furthermore, the user of the remote computing system 8 is able to use the remote computing system 8 to submit the electronic 3D models to the computing system 4 for analysis.

In some embodiments, the remote computing system 8 submits the electronic 3D models via the network 12. The computing system 4 comprises a network interface 14 that receives the electronic 3D models from the network 12.

In some embodiments, the user of the remote computing system 8 stores the electronic 3D models to an optical disc. The user of the remote computing system 8 then submits the electronic 3D models by sending the optical disc to a user of the computing system 4. The computing system 4 comprises an optical media interface 16 that receives and reads electronic 3D models stored on the optical disc. Example types of optical discs include CD-ROMs, DVDs, BluRay discs, Mini-Discs, HD DVD discs, and so on.

In some embodiments, the user of the remote computing system 8 stores the electronic 3D models to an external device. The user of the remote computing system 8 then submits electronic 3D models by sending the external device to a user of the computing system 4. The computing system 4 comprises an external device interface 18 that reads the electronic 3D models stored on the external device. Example types of external devices include USB flash memory devices, memory sticks, CompactFlash cards, Multimedia Cards, SD Cards, xD Picture cards, and so on.

As described in detail herein, the computing system 4 enables a user to analyze submitted electronic 3D models to determine difficulties of orthodontic treatment. In various embodiments, the computing system 4 enables various users to analyze submitted electronic 3D models. For example, in some embodiments, the computing system 4 enables a user of the computing system 4 to analyze submitted electronic 3D models. Furthermore, in some embodiments, the computing system 4 enables a user of the remote computing system 6 to analyze submitted electronic 3D models. In such embodiments, the remote computing system 6 and the computing system 4 communicate information about submitted electronic 3D models via the network 12. For example, the remote computing system 6 can download electronic 3D models from the remote computing system 6. In this example, the test can be performed at the remote computing system 6. In another example, a web browser application operates on the remote computing system 6. In this example, the user of the remote computing system 6 uses the web browser application to access web pages generated by the computing system 4. The web pages allow the user of the remote computing system 6 to view the electronic 3D models and to provide input to the computing system 4.

Figure 2:
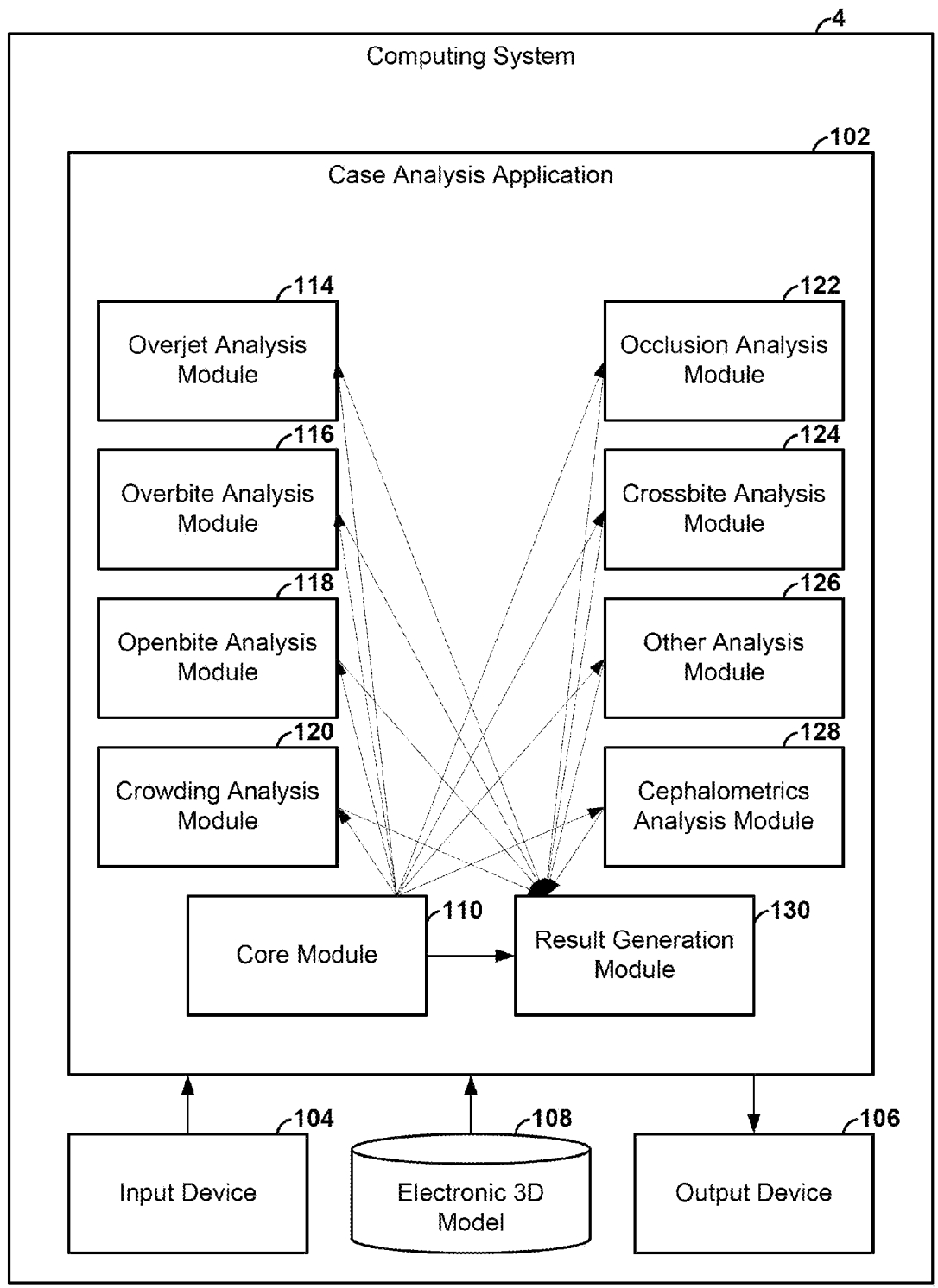
FIG. 2 is a block diagram illustrating example logical components of a computing device.

FIG. 2 is a block diagram illustrating example logical components of a computing system 4. As illustrated in the example of FIG. 2, the logical components of the computing system 4 include a case analysis application 102, an input device 104, an output device 106, and an electronic 3D model 108. It should be appreciated that the computing system 4 illustrated in the example of FIG. 2 is merely one embodiment. Other embodiments include more, fewer, or different logical components than those shown in the example of FIG. 2.

The case analysis application 102 is a user application for evaluating the difficulty of orthodontic treatment of a person's dentition. In various embodiments, the case analysis application 102 is implemented in various ways. For example, in some embodiments, the case analysis application 102 is implemented using a set of software instructions that, when executed by a processing unit of the computing system 4, cause the computing system 4 to provide the case analysis application 102. In other embodiments, the computing system 4 comprises one or more application specific integrated circuits (ASICs) that operate to cause the computing system 4 to provide the case analysis application 102.

The input device 104 is a device that enables the computing system 4 to receive input from a user. In various embodiments, the input device 104 is implemented in various ways. For example, in various embodiments, the input device 104 can be implemented by a mouse, a trackball, a touch screen, an infrared remote control, a keyboard, a keypad, a joystick, a microphone, or another type of device that enables the computing system 4 to receive input from a user. Furthermore, in some embodiments, the input device 104 is implemented as a network interface card or a modem. In such embodiments, a user uses another computing device remote from the computing system 4 to send input to the computing device via an electronic communication network. In such embodiments, the input device 104 receives input indirectly from the user.

The output device 106 is a device that enables the computing system 4 to output data. In various embodiments, the output device 106 is implemented in various ways. For example, the output device 106 can be implemented as a computer monitor, a television set, a touch screen, or another type of device that enables the computing system 4 to output data. It should be appreciated that in some embodiments where the output device 106 is a touch screen, the output device 106 and the input device 104 are the same device. Furthermore, in some embodiments, the output device 106 is implemented as a network interface card or a modem. In such embodiments, a user uses another computing device remote from the computing system 4 (e.g., remote computing system 6) to view information sent by the computing system 4 via an electronic communication network (e.g., network 12).

The electronic 3D model 108 is a set of data representing a before model of a patient's dentition. In some embodiments, the electronic 3D model 108 represents a real patient's dentition. In other embodiments, the electronic 3D model 108 represents an imaginary patient's dentition. In various embodiments, the electronic 3D model 108 is implemented in various ways. For example, in some embodiments, the electronic 3D model 108 is implemented as a computer file. In other example embodiments, the electronic 3D model 108 is implemented as one or more records in a relational database. The electronic 3D model 108 is stored on one or more computer-readable data storage media. A computer-readable data storage medium is a physical device or article of manufacture that stores data. Example types of computer-readable data storage media include hard disks, optical drives, read-only memory (ROM) units, random-access memory (RAM) units, solid state memory drives (e.g., Flash memory), magnetic tape drives, floppy disks, and other types of physical devices and articles of manufacture that store data. Although the example of FIG. 2 shows the computing system 4 as containing the electronic 3D model 108, it should be appreciated that in other embodiments, some or all of the electronic 3D model 108 is stored at one or more other computing devices electronically accessible to the computing system 4.

The American Board of Orthodontics (ABO) evaluates the difficulty of treating a patient based on several categories. These categories are: the patient's overjet, the patient's overbite, the patient's openbite, the patient's crowding, the patient's occlusion, the patient's crossbite, other characteristics of the patient, and the patient's cephalometrics. Each of these categories is assigned a score based on an analysis of the patient's characteristics in each of these categories. The difficulty of treating the patient is the total of the scores assigned to each of the categories. As used herein, the total of the scores assigned to each of the categories is referred to as the case score. If the patient's case score is not sufficiently high, the patient is deemed to be too easy to treat. Therefore, the ABO does not consider cases with case scores below a certain threshold.

A user uses the case analysis application 102 to analyze the difficulty of treating a patient. In various embodiments, the user can be various types of people. For example, in some embodiments, the user is an orthodontist who wants to analyze the difficulty of treating a patient prior to submitting models of the orthodontic patient's dentition to the ABO. In other embodiments, the user is a technician who analyzes the difficulty of treating patients on behalf of orthodontists, on behalf of the ABO, or on behalf of one or more other entities.

As illustrated in the example of FIG. 2, the case analysis application 102 comprises a core module 110, an overjet analysis module 114, an overbite analysis module 116, an openbite analysis module 118, a crowding analysis module 120, an occlusion analysis module 122, a crossbite analysis module 124, an other analysis module 126, a cephalometrics analysis module 128, and a result generation module 130. Although FIG. 2 shows each of the modules of the case analysis application 102 within the computing system 4, it should be appreciated that, in other embodiments, the modules of the case analysis application 102 are distributed among one or more computing devices that are in electronic communication with one another.

The core module 110 causes the output device 106 to display a graphical user interface. The graphical user interface comprises controls that enable the user to select an electronic 3D model for analysis and to perform an analysis on the selected electronic 3D model. When a user selects the electronic 3D model 108, the core module 110 loads the electronic 3D model 108.

The overjet analysis module 114 assists the user in performing an analysis of the patient's overjet. The overbite analysis module 116 assists the user in performing an analysis of the patient's overbite. The openbite analysis module 118 assists the user in performing an analysis of the patient's openbite. The crowding analysis module 120 assists the user in performing an analysis of the patient's crowding. The occlusion analysis module 122 assists the user in performing an analysis of the patient's occlusion. The crossbite analysis module 124 assists the user in performing an analysis of the patient's crossbite. The other analysis module 126 assists the user in performing an analysis of other characteristics of the patient. The cephalometrics analysis module 128 assists the user in performing an analysis of the patient's cephalometrics.

The result generation module 130 generates a case score based on the analysis of the patient's overjet, the analysis of the patient's overbite, the analysis of the patient's openbite, the analysis of the patient's crowding, the analysis of the patient's occlusion, the analysis of the patient's crossbite, the analysis of the patient's other characteristics, and the analysis of the patient's cephalometrics.

Furthermore, in some embodiments, the result generation module 130 generates an output file containing the case score. In various embodiments, the output file has various types of content. For example, in some embodiments, the output file comprises scores resulting from the analysis of the patient's overjet, the analysis of the patient's overbite, the analysis of the patient's openbite, the analysis of the patient's crowding, the analysis of the patient's occlusion, the analysis of the patient's crossbite, the analysis of the patient's other characteristics, and the analysis of the patient's cephalometrics. In other embodiments, the output file also includes additional information about how these scores are derived. Furthermore, in various embodiments, the output file is formatted in various ways. For example, in some embodiments, the output file is formatted as a text file. In other embodiments, the output file is formatted as one or more database records. In yet other embodiments, the output file is a Hypertext Markup Language (HTML) file. In yet other embodiments, the output file is an Extensible Markup Language (XML) file.

Figure 3:
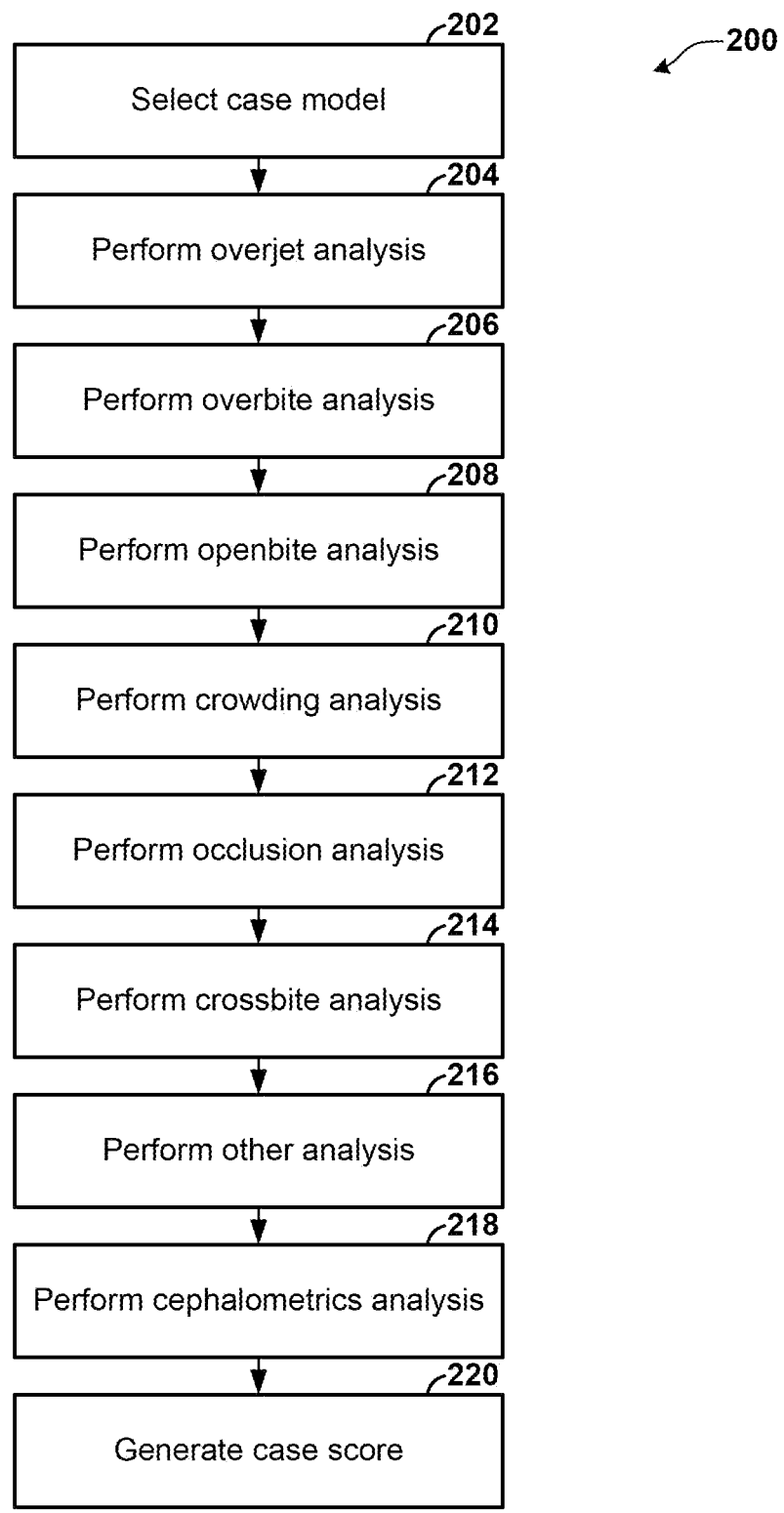
FIG. 3 is a flowchart illustrating an example operation performed by a user to identify a patient's case score.

FIG. 3 is a flowchart illustrating an example operation 200 performed by a user to identify a patient's case score. It should be appreciated that the operation 200 merely represents one example operation to determine a patient's case score. In other embodiments, operations to determine a patient's case score involve more, fewer, or different steps or include the steps of the operation 200 in different orders.

As illustrated in the example of FIG. 3, the operation 200 begins when the user selects the electronic 3D model 108 (202). After the core module 110 loads the electronic 3D model 108, the user uses the overjet analysis module 114 to perform an analysis of the patient's overjet (204). The analysis of the patient's overjet generates the patient's overjet score. The user uses the overbite analysis module 116 to perform an analysis of the patient's overbite (206). The analysis of the patient's overbite score generates the patient's overbite score. Next, the user uses the openbite analysis module 118 to perform an analysis of the patient's openbite (208). The analysis of the patient's openbite score generates the patient's openbite score.

The user uses the crowding analysis module 120 to perform an analysis of the patient's dental crowding (210). The analysis of the patient's dental crowding generates the patient's crowding score. In various embodiments, the user uses the crowding analysis module 120 to perform the analysis of the patient's dental crowding in various ways. For example, in some embodiments, the user uses the operation 300 illustrated in the example of FIG. 4 to perform the analysis of the patient's dental crowding.

Subsequently, the user uses the occlusion analysis module 122 to perform an analysis of the patient's occlusion (212). The analysis of the patient's occlusion generates the patient's final occlusion score. In some embodiments, the patient's final occlusion score indicates a severity of malocclusion. In various embodiments, the user uses the occlusion analysis module 122 to perform the analysis of the patient's occlusion in various ways. For example, in some embodiments, the user uses the operation 800 illustrated in the example of FIG. 9 to perform the analysis of the patient's occlusion.

The user then uses the crossbite analysis module 124 to perform an analysis of the patient's crossbite (214). The analysis of the patient's crossbite generates the patient's crossbite score. Next, the user uses the other analysis module 126 to perform an analysis of other characteristics of the patient (216). The analysis of the patient's other characteristics generates the patient's other characteristics score. The user then uses the cephalometrics analysis module 128 to perform a cephalometrics analysis of the patient (218). The analysis of the patient's cephalometrics generates the patient's cephalometrics score.

The user then uses the result generation module 130 to generate the patient's case score (220). The patient's case score is based on the analysis of the patient's overjet score, the patient's overbite score, the patient's openbite score, the patient's crowding score, the patient's occlusion score, the patient's crossbite score, the patient's other characteristics score, and the patient's cephalometrics score. In various embodiments, the result generation module 130 generates the patient's case score in various ways. For example, in some embodiments, the result generation module 130 generates the patient's case score by adding together the patient's overjet score, the patient's overbite score, the patient's openbite score, the patient's crowding score, the patient's occlusion score, the patient's crossbite score, the patient's other characteristics score, and the patient's cephalometrics score.

Figure 4:
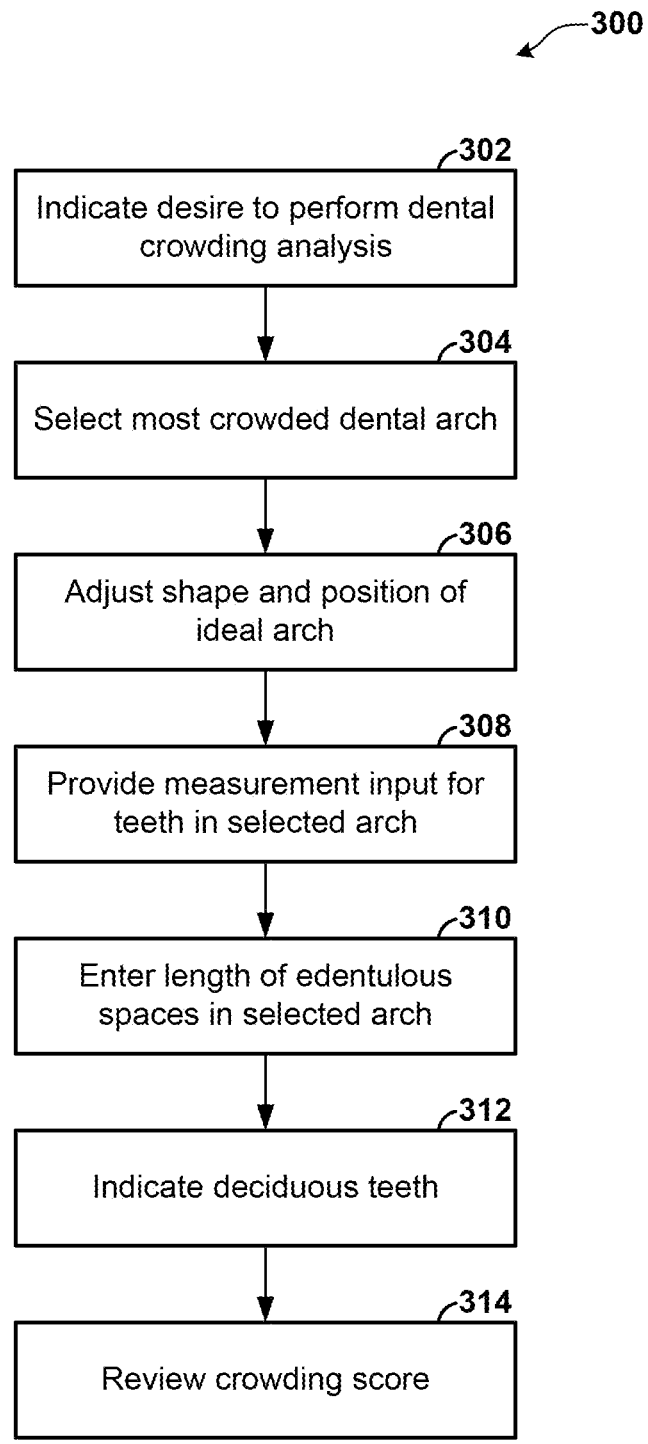
FIG. 4 is a flowchart illustrating an example operation performed by a user of a case analysis application to perform a dental crowding analysis.

FIG. 4 is a flowchart illustrating an example operation 300 performed by a user of the case analysis application 102 to perform a dental crowding analysis. It should be appreciated that the operation 300 merely represents one example operation to perform a crowding analysis. In other embodiments, operations to perform a dental crowding analysis involve more, fewer, or different steps or include the steps of the operation 300 in different orders.

As illustrated in the example of FIG. 4, the operation 300 begins when the user interacts with a user interface of the case analysis application 102 to indicate that the user desires to perform a dental crowding analysis for a patient (302). In various embodiments, the user interacts with the user interface of the case analysis application 102 to indicate that the user desires to perform a dental crowding analysis in various ways. For example, in some embodiments, the user interface includes a set of controls. Each of the controls includes a separate control for each type of analysis. For instance, the set of controls includes controls for overjet, overbite, openbite, crowding, occlusion, crossbite, other, and cephalometrics. In such embodiments, the user interacts with the user interface to indicate that the user wants to perform a dental crowding analysis by selecting the control for crowding.

In response to the user indicating that the user wants to perform a dental crowding analysis, the crowding analysis module 120 causes the output device 106 to display a 3D model of the patient's maxillary dental arch and a 3D model of the patient's mandibular dental arch within the user interface of the case analysis application 102. In some embodiments, the user can rotate, tumble, pan, zoom, or otherwise change a point of view of the 3D model. The user then selects the most crowded one of the patient's dental arches (304). In response to the user selecting the most crowded one of the patient's dental arches, the crowding analysis module 120 causes the output device 106 to display a 3D model of the most crowded one of the patient's dental arches within the user interface of the case analysis application 102. For ease of explanation, the most crowded one of the patient's dental arches is referred to herein as the selected arch.

An ideal arch is superimposed on the 3D model of the selected arch. In some embodiments, the crowding analysis module 120 automatically identifies a midline of the selected arch. The crowding analysis module 120 automatically superimposes the ideal arch on the 3D model of the selected arch such that the midline of the ideal arch is the same as the automatically identified midline of the selected arch. The user adjusts the shape and position of the ideal arch such that the ideal arch has a desired shape (306). The desired shape of the ideal arch indicates where the patient's teeth in the selected arch should be positioned when orthodontic treatment is complete. As the user adjusts the shape and position of the ideal arch, the crowding analysis module 120 causes the output device 106 to display the current shape of the ideal arch.

In some embodiments, multiple adjustment points are displayed on the ideal arch. The positions of the adjustment points define the shape of the ideal arch. In other words, the ideal arch forms a smooth arc that passes through each of the adjustment points. The user adjusts the shape and position of the ideal arch by clicking on various ones of the adjustment points and dragging the adjustment points to different positions. In other words, the user drags-and-drops adjustment points to adjust the shape of the ideal arch. The crowding analysis module 120 automatically adjusts the shape of the ideal arch such that the shape of the ideal arch is still defined by the adjusted positions of the adjustment points.

Furthermore, in some embodiments where the adjustment points are displayed on the ideal arch, the adjustment points are symmetrically disposed on opposite sides of the midline of the ideal arch. When the user adjusts the shape of the ideal arch by adjusting a position of a given one of the adjustment points, the crowding analysis module 120 automatically adjusts the position of a corresponding adjustment point. The corresponding adjustment point is symmetrically disposed on the opposite side of the midline of the ideal arch from the given adjustment point. The crowding analysis module 120 adjusts the position of the corresponding adjustment point such that the corresponding adjustment point remains at a position symmetrically disposed on the opposite side of the midline of the ideal arch from the given adjustment point. Because the shape of the ideal arch is defined by the positions of the adjustment points, the crowding analysis module 120 adjusts the shape of the ideal arch. In this way, the ideal arch automatically stays symmetrical.

In some embodiments, the user is able to instruct the crowding analysis module 120 not to automatically adjust the position of the symmetrically positioned adjustment point. For example, the user may hold down a control key while dragging an adjustment point to instruct the crowding analysis module 120 not to automatically adjust the position of the symmetrically positioned adjustment point. In this way, the user is able to adjust a single one of the adjustment points, thereby causing the ideal arch to be asymmetrical.

In some embodiments, the crowding analysis module 120 estimates, prior to receiving adjustment input from the user, where the patient's teeth in the selected arch should be located after orthodontic treatment. The crowding analysis module 120 then generates the ideal arch such that the ideal arch passes through the estimated locations of the patient's teeth after orthodontic treatment. In various embodiments, the crowding analysis module 120 uses various algorithms to estimate where the patient's teeth should be located after orthodontic treatment. For example, the crowding analysis module 120 can estimate where the patient's teeth should be located by aligning centroids within regions in the selected arch. In another example, the crowding analysis module 120 can estimate where the patient's teeth should be located based on a midline of the gum tissue of the selected arch.

After the user has finished adjusting the shape and position of the ideal arch, the user provides a measurement input for teeth in the selected arch (308). For instance, in some embodiments, the user provides a measurement input for each non-molar tooth in the selected arch. The measurement input for a tooth indicates two points. A line between the two points approximately coincides with the ideal arch following successful treatment of the patient. For example, the line between the two points may substantially overlap with the ideal arch following treatment of the patient.

In various embodiments, the user provides the measurement input in various ways. For example, in some embodiments, the user provides the measurement input for a tooth by pressing a button when a cursor is at a position corresponding to one end of the tooth and then pressing the button again when the cursor is at a position corresponding to an opposite end of the tooth. The user repeats this for other teeth in the selected arch, such as each non-molar tooth in the selected arch. In other embodiments, the user provides the measurement input for a tooth by depressing a button when a cursor is at a position corresponding to one end of the tooth and releasing the button when the cursor is at a position corresponding to an opposite end of the tooth. The user repeats this for other teeth in the selected arch.

Next, the user provides input to the case analysis application 102 indicating a length of edentulous spaces in the selected dental arch (310). An edentulous space is a space in an arch where a tooth is missing. For example, if the selected arch is missing two teeth and the combined width of the missing teeth is 12.7 millimeters, the user provides input to the case analysis application 102 indicating that the length of edentulous spaces in the selected dental arch is 12.7 millimeters. When the user enters a length of edentulous spaces, the crowding analysis module 120 calculates a tooth width total based on the tooth widths and the length of the edentulous spaces.

Furthermore, the user provides input to the case analysis application 102 indicating deciduous teeth in the selected dental arch (312). Deciduous teeth are typically smaller than permanent teeth. A proper treatment plan should take the larger size of the permanent teeth into account. The amount of space needed for permanent teeth is generally related to sizes of corresponding deciduous teeth according to known ratios. For example, Moyer's analysis or the Tanaka-Johnson analysis can be used to predict space requirements for adult dentition. When the user indicates that a tooth is a deciduous tooth, the crowding analysis module 120 calculates an expected amount of space needed for a permanent replacement tooth corresponding to the deciduous tooth. The crowding analysis module 120 calculates a total of the tooth widths using the expected amount of space needed for the permanent replacement tooth instead of the tooth width for the deciduous tooth.

After the user indicates to the case analysis application 102 which of the teeth are deciduous teeth, the user reviews a crowding score for the patient (314). The crowding analysis module 120 calculates the crowding score for the patient based, at least in part, on a comparison of the length of the ideal arch and a total of the tooth widths. In some embodiments, the user reviews the crowding score for the patient when the crowding analysis module 120 causes the output device 106 to display the crowding score.

Figure 5:
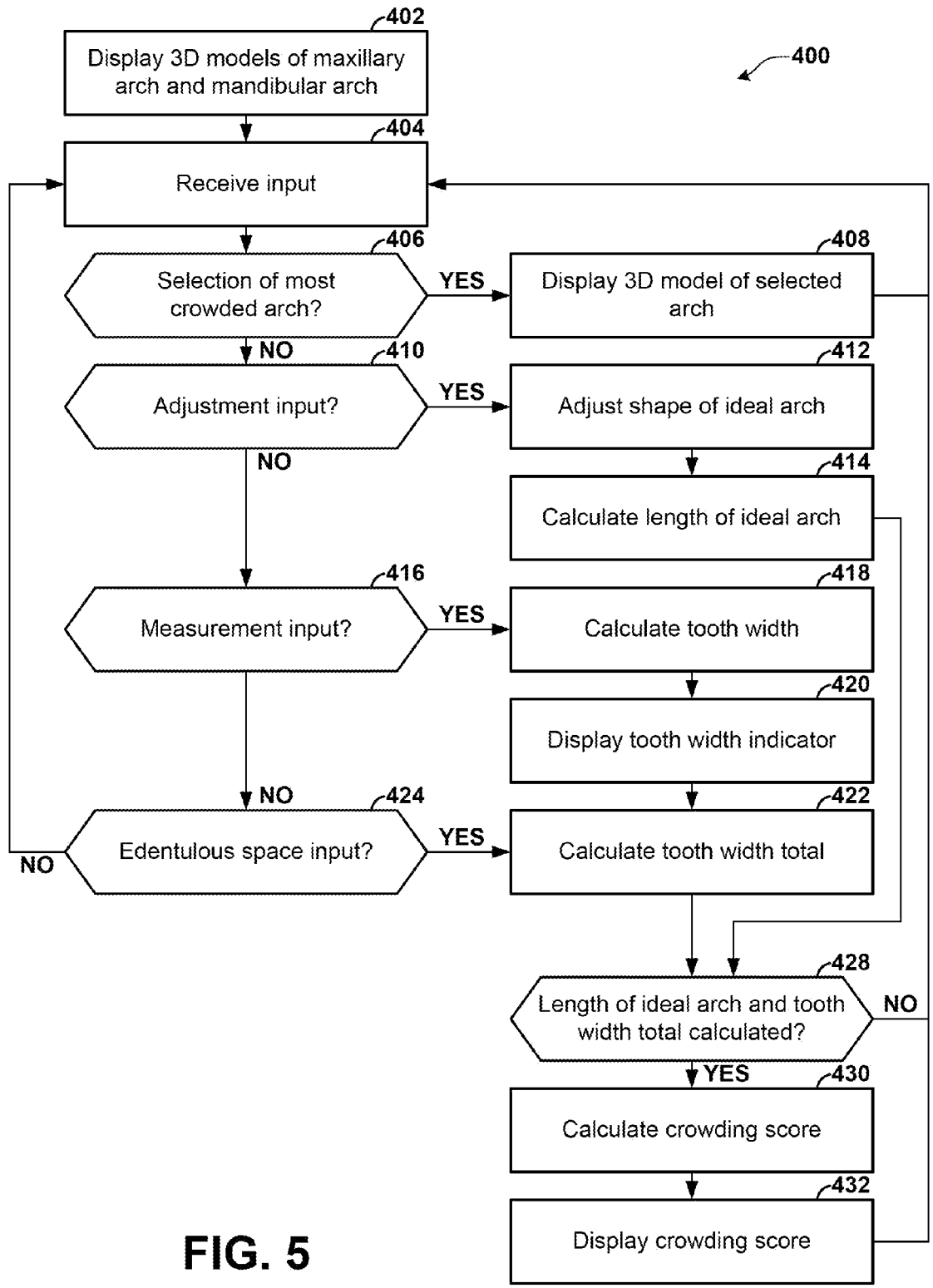
FIG. 5 is a flowchart illustrating an example operation performed by a crowding analysis module to perform a dental crowding analysis.

FIG. 5 is a flowchart illustrating an example operation 400 performed by the crowding analysis module 120 to perform a dental crowding analysis. It should be appreciated that the operation 400 merely represents one example operation to perform a dental crowding analysis. In other embodiments, operations to perform a dental crowding analysis involve more, fewer, or different steps or include the steps of the operation 400 in different orders.

As illustrated in the example of FIG. 5, the operation 400 begins when the crowding analysis module 120 causes the output device 106 to display a 3D model of the patient's maxillary arch and a 3D model of the patient's mandibular arch within the user interface of the case analysis application 102 (402).

Subsequently, the crowding analysis module 120 receives input from the user of the case analysis application 102 (404). As described below, the crowding analysis module 120 performs various actions in response to receiving the input.

Upon receiving the input, the crowding analysis module 120 determines whether the input is a selection of a most crowded dental arch (406). If the input is a selection of the most crowded arch ("YES" of 406), the crowding analysis module 120 causes the output device 106 to display a 3D model of the selected arch within the user interface of the case analysis application 102 (408). The crowding analysis module 120 is then able to receive additional input (404). In some embodiments, an ideal arch is superimposed over the 3D model of the selected arch. In other embodiments, the ideal arch is superimposed over the 3D model of the selected arch in response to an additional user input. Furthermore, in some embodiments, the crowding analysis module 120 identifies a midline of the selected dental arch. In such embodiments, the crowding analysis module 120 causes the output device 106 to display the ideal arch superimposed on the 3D model of the selected dental arch such that a midline of the ideal arch coincides with the identified midline of the dental arch.

If the input is not a selection of the most crowded arch ("NO" of 406), the crowding analysis module 120 determines whether the input is an adjustment input (410). The adjustment input indicates an adjustment to the ideal arch. If the input is an adjustment input ("YES" of 410), the crowding analysis module 120 adjusts the shape of the ideal arch in accordance with the adjustment input and displays the adjusted ideal arch (412). After adjusting the shape of the ideal arch, the crowding analysis module 120 calculates a length of the ideal arch (414).

If the input is not an adjustment input ("NO" of 410), the crowding analysis module 120 determines whether the input is a measurement input for a tooth (416). The measurement input for a tooth indicates two points on the tooth. Following successful treatment of the patient, a line between the two points on the tooth should coincide with the ideal arch.

If the input is a measurement input ("YES" of 416), the crowding analysis module 120 calculates a tooth width for the tooth (418). In various embodiments, the crowding analysis module 120 calculates the tooth width for the tooth in various ways. For example, the crowding analysis module 120 can calculate the tooth width for the tooth by calculating a distance between projected points for the tooth. The projected points for the tooth are points projected onto a plane parallel to an occlusal plane of the patient by the points indicated by the measurement input for the tooth. The crowding analysis module 120 displays then a tooth width indicator for the tooth (420). The tooth width indicator is superimposed on the 3D model of the selected arch. In some embodiments, the tooth width indicator for the tooth comprises a line between the two points indicated by the measurement input for the tooth. Furthermore, in some embodiments, the tooth width indicator for the tooth indicates the distance between of the two points indicated by the measurement input for the tooth.

If the input is not a tooth measurement input ("NO" of 416), the crowding analysis module 120 determines whether the input is an edentulous space input (424). The edentulous space input indicates a length of edentulous spaces in the selected arch. If the input is not an edentulous space input ("NO" of 424), the crowding analysis module 120 may ignore the input and is able to receive another input (404), and the operation 400 recurs.

After displaying a tooth width indicator in step 422 or after determining that the input is an edentulous space input ("YES" of 424), the crowding analysis module 120 calculates a tooth width total (422). The tooth width total is based on the tooth widths plus a length of the edentulous spaces in the selected arch. In various embodiments, the crowding analysis module 120 calculates the tooth width total in various ways. For example, in some embodiments, the crowding analysis module 120 calculates the tooth width total by adding together the tooth widths and the length of the edentulous space. Furthermore, in some embodiments, the tooth measurement input indicates whether the tooth is a deciduous tooth. If the tooth measurement input indicates that the tooth is a deciduous tooth, the crowding analysis module 120 calculates an expected width of a replacement permanent tooth corresponding to the deciduous tooth. The crowding analysis module 120 calculates the tooth width total by adding together the tooth widths for each of the non-molar teeth, using the expected width of the replacement permanent tooth instead of the tooth width of the deciduous tooth.

After either calculating the length of the ideal arch in step 414 or calculating a tooth width total in step 422, the crowding analysis module 120 determines whether the length of the ideal arch and the total of the tooth widths have been calculated (428). If both the length of the ideal arch and the tooth width total have been calculated ("YES" of 428), the crowding analysis module 120 calculates the patient's crowding score (430). In various embodiments, the crowding analysis module 120 calculates the patient's crowding score in various ways. For example, in some embodiments, the crowding analysis module 120 calculates the patient's crowding score based on a ratio of the length of the ideal arch compared to the tooth width total.

After calculating the patient's crowding score, the crowding analysis module 120 causes the output device 106 to display the patient's crowding score within the user interface of the case analysis application 102 (432). The crowding analysis module 120 may then receive additional input (404) and the operation 400 recurs.

Figure 6:
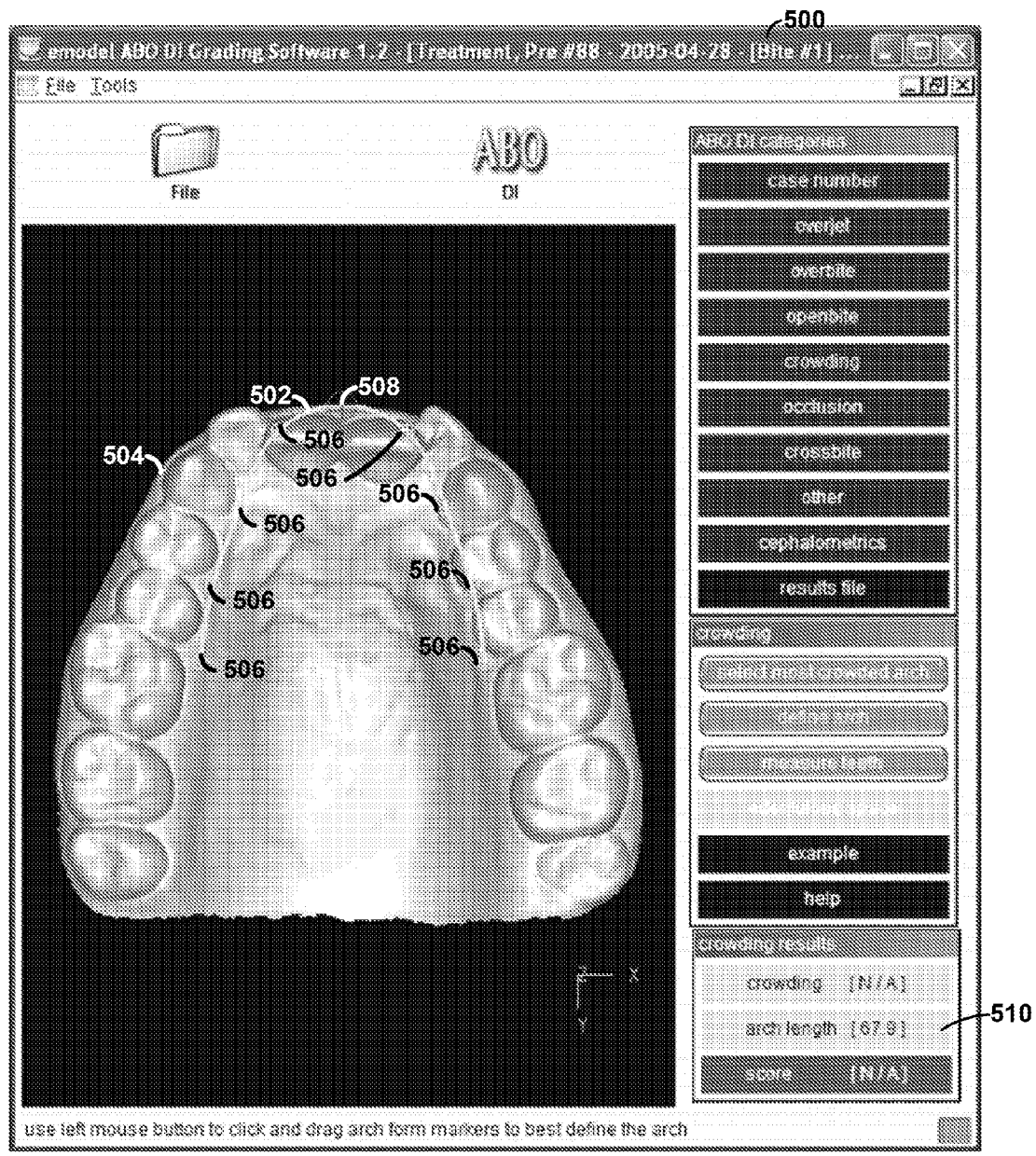
FIG. 6 is an example screen illustration showing a user interface of a case analysis application containing an ideal arch superimposed on an electronic 3D model of a dental arch.

FIG. 6 is an example screen illustration showing a user interface 500 of the case analysis application 102 containing an ideal arch 502 superimposed on a 3D model 504 of a dental arch. Initially, the ideal arch 502 does not indicate where the teeth in the arch should be positioned when orthodontic treatment is complete. As illustrated in the example of FIG. 6, the ideal arch 502 includes a set of adjustment points 506. The adjustment points 506 are symmetrically disposed on opposing sides of the midline of the ideal arch 502. In some embodiments, the user adjusts the shape of the ideal arch 502 by dragging individual ones of the adjustment points 506. Furthermore, the user is able to reposition the ideal arch 502 by dragging a midline adjustment point 508.

The user interface 500 also contains an arch length feature 510 that indicates a length of the ideal arch 502. In the example of FIG. 6, the arch length feature 510 indicates that the length of the ideal arch 502 is 67.9 millimeters.

Figure 7:
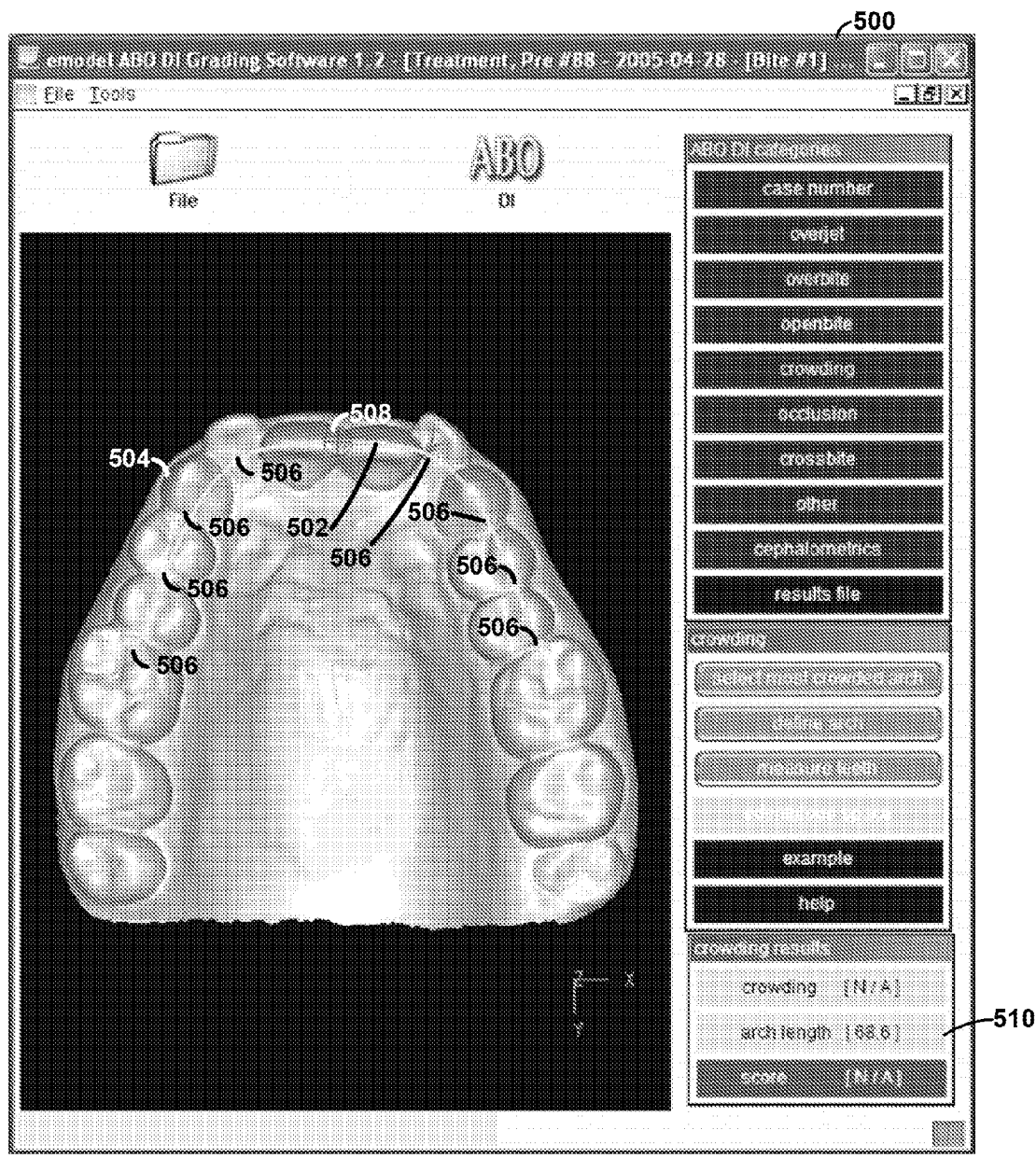
FIG. 7 is an example screen illustration showing the user interface in which the ideal arch has been adjusted.

FIG. 7 is an example screen illustration showing the user interface 500 in which the ideal arch 502 has been adjusted. In the example of example of FIG. 7, the user interface 500 contains the 3D model 504 of the dental arch shown in FIG. 6. However, the ideal arch 502 has been adjusted such that the ideal arch 502 indicates where the teeth in the dental arch should be positioned when orthodontic treatment is complete.

The user interface 500 contains the arch length feature 510. However, in the example of FIG. 7, the arch length feature 510 indicates that the length of the ideal arch 502 is 68.6 millimeters. The length of the ideal arch 502 is longer in the example of FIG. 7 because the user has adjusted the ideal arch 502 to widen the ideal arch 502.

Figure 8:
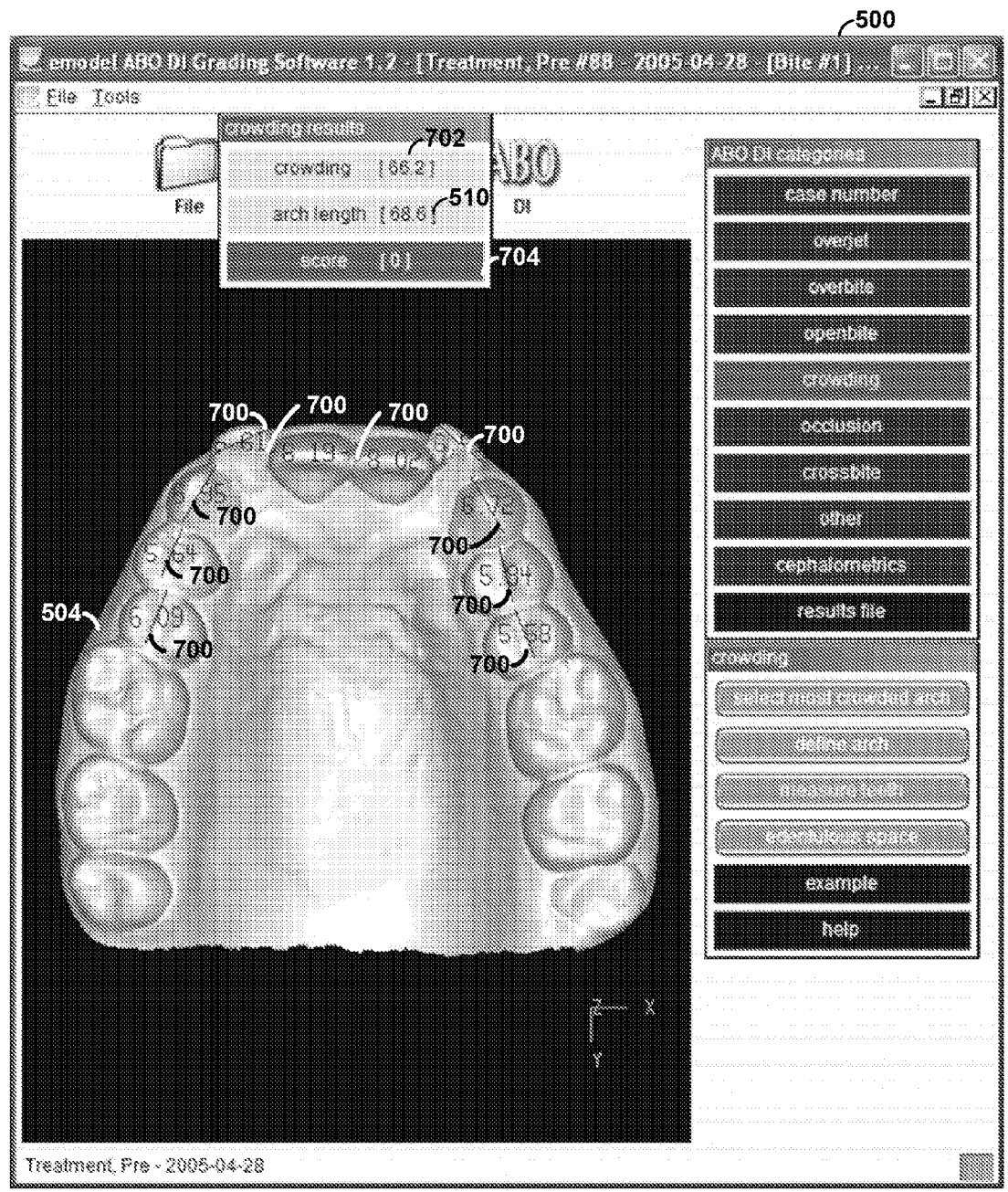
FIG. 8 is an example screen illustration showing the user interface in which the user has provided measurement input for teeth on the electronic 3D model of the dental arch.

FIG. 8 is an example screen illustration showing the user interface 500 in which the user has provided measurement input for each non-molar tooth in the 3D model 504 of the dental arch. Because the user has provided measurement input for each non-molar tooth, the user interface 50 contains tooth width indicators 700 on each of the pre-molar teeth. Each of the tooth width indicators 700 indicates a width of a tooth. For example, the width of the right maxillary second premolar is 5.68 millimeters.

The user interface 500 also contains a crowding feature 702. The crowding feature 702 indicates a tooth width total for the patient. In the example of FIG. 8, the crowding feature 702 indicates that the total width of each of the teeth is 66.2 millimeters. 66.2 is the sum of 6.09+5.64+9.95+6.61+8.19+ 8.02+6.51+6.72+5.84+58.58 rounded to the nearest tenth of a millimeter. The example of FIG. 8 also shows the arch length feature 510 adjacent to the crowding feature 702. Because the arch length feature 510 is adjacent to the crowding feature 702, it may be easy for a user to compare the length of the ideal arch with the tooth width total.

In addition, the user interface 500 contains a crowding score feature 704. The crowding score feature 704 indicates the patient's crowding score. In the example of FIG. 8, the crowding score feature 704 indicates that the crowding score is zero. The crowding score is zero because the arch length is greater than the total width total.

Figure 9:
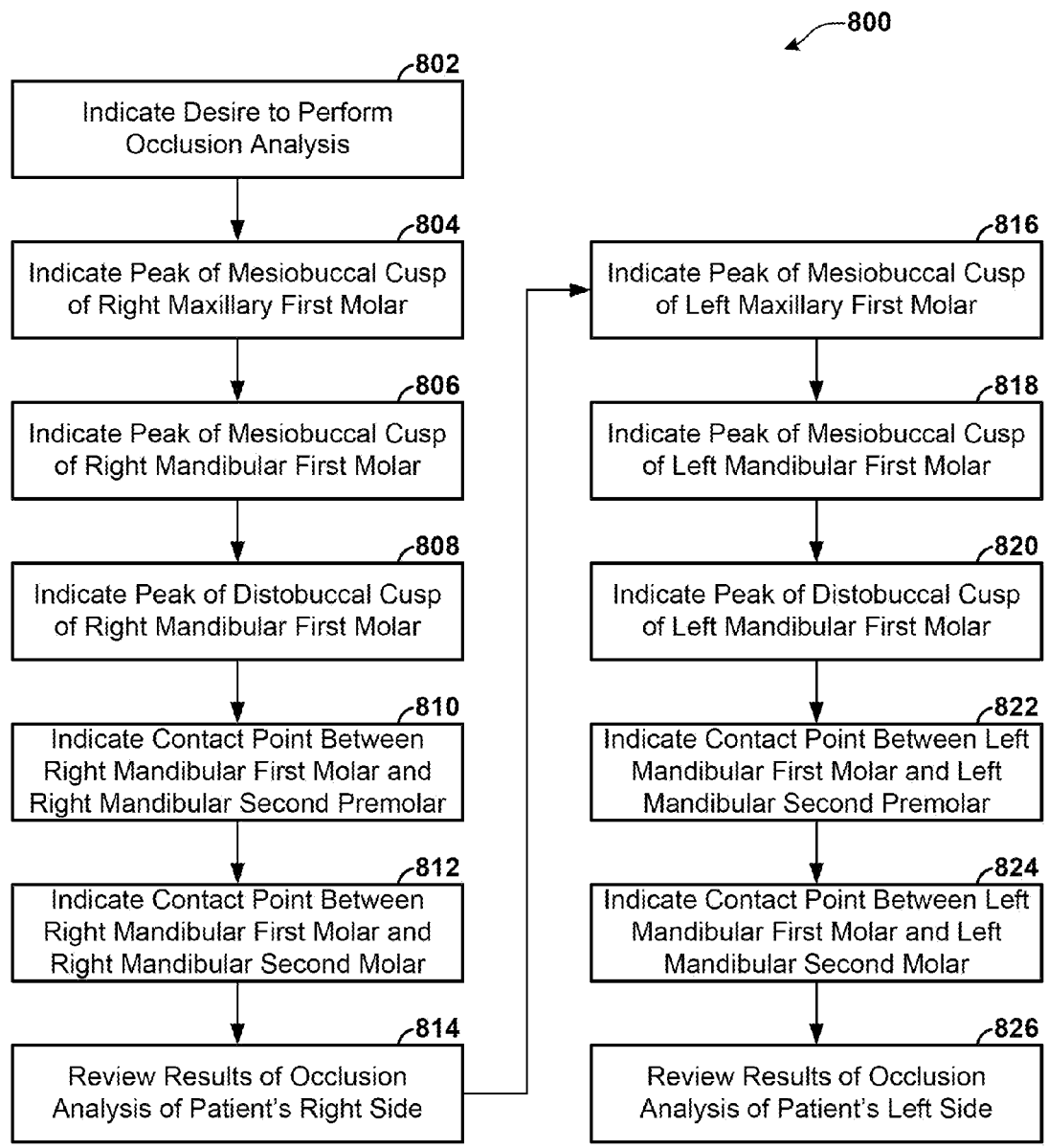
FIG. 9 is a flowchart illustrating an example operation performed by the user to perform an occlusion analysis.

FIG. 9 is a flowchart illustrating an example operation 800 performed by a user to perform an occlusion analysis. It should be appreciated that the operation 800 merely represents one example operation performed by a user to perform an occlusion analysis. In other embodiments, other operations involve more, fewer, or different steps or include the steps of the operation 800 in different orders.

As illustrated in the example of FIG. 9, the user interacts with the user interface of the case analysis application 102 to indicate that the user wants to perform an occlusion analysis for a patient (802). In various embodiments, the user interacts with the user interface of the case analysis application 102 to indicate that the user wants to perform an occlusion analysis in various ways. For example, in some embodiments, the user interface includes a set of controls. Each of the controls includes a separate control for each phase of a case analysis. For instance, the set of controls includes controls for overjet, overbite, openbite, crowding, occlusion, crossbite, other, and cephalometrics. In such embodiments, the user interacts with the user interface to indicate that the user wants to perform an occlusion analysis by selecting the control for occlusion.

When the user interacts with the user interface to indicate that the user wants to perform an occlusion analysis, the occlusion analysis module 122 causes the output device 106 to display a 3D model of at least a portion of the patient's right maxillary arch within the user interface. The user is able to rotate, pan, zoom in on, zoom out from, tumble, or otherwise change a point of view of the 3D model to obtain a desired view. The user indicates a point on the 3D model of the patient's right maxillary arch corresponding to the peak of the mesiobuccal cusp of the patient's right maxillary first molar (804). In various embodiments, the user indicates the point corresponding to the peak of the mesiobuccal cusp of the patient's right maxillary first molar in various ways. For example, in some embodiments, the user positions a mouse cursor over the point corresponding to the peak of the mesiobuccal cusp of the patient's right maxillary first molar and then clicks a mouse button.

After the user indicates the point corresponding to the peak of mesiobuccal cusp of the patient's right maxillary first molar, the occlusion analysis module 122 causes the output device 106 to display a 3D model of at least a portion of the patient's right mandibular arch within the user interface. The user is able to tumble, rotate, pan, zoom in on, zoom out from, or otherwise manipulate a point of view of the 3D model of the patient's right mandibular arch to obtain a desired view of the patient's right mandibular arch. The user then indicates a point on the 3D model of the patient's right mandibular arch corresponding to a peak of the mesiobuccal cusp of the patient's right mandibular first molar (806). Next, the user indicates a point on the 3D model of the patient's right mandibular arch corresponding to a peak of the distobuccal cusp of the patient's right mandibular first molar (808). The user then indicates a point on the 3D model of the patient's right mandibular arch corresponding to a contact point between the patient's right mandibular first molar and the patient's right mandibular second premolar (810). Next, the user indicates a point on the 3D model of the patient's right mandibular arch corresponding to a contact point between the patient's right mandibular first molar and the patient's right mandibular second molar (812). For ease of explanation, the points corresponding to the mesiobuccal cusp of the patient's right mandibular first molar, the distobuccal cusp of the patient's right mandibular first molar, the contact between the patient's right mandibular first molar and the patient's right mandibular second premolar, and the contact between the patient's right mandibular first molar and the patient's right mandibular second molar are referred to herein as the relevant points on the patient's right mandibular first molar.

The user is then able to review the results of the occlusion analysis of the patient's right side (814). In various embodiments, the user is able to review the results of the occlusion analysis of the patient's right side in various ways. For example, in some embodiments, the occlusion analysis module 122 causes the output device 106 to display the patient's right side occlusion score within the user interface of the case analysis application 102. Furthermore, in some embodiments, the occlusion analysis module 122 causes the output device 106 to display one or more features superimposed on the 3D model of the patient's right mandibular arch. The features indicate to the user how the occlusion analysis module 122 identified the patient's right side occlusion score.

After the user reviews the results of the occlusion analysis of patient's right side, the occlusion analysis module 122 causes the output device 106 to display a 3D model of at least a portion of the patient's left maxillary arch. The user is able to tumble, rotate, pan, zoom in on, zoom out from, or otherwise manipulate the view point of the 3D model of the patient's left maxillary arch to obtain a desired view of the patient's left maxillary arch. The user indicates a point on the 3D model of the patient's left maxillary arch corresponding to the peak of the mesiobuccal cusp of the patient's left maxillary first molar (816).

After the user indicates the point corresponding to the peak of mesiobuccal cusp of the patient's left maxillary first molar, the occlusion analysis module 122 causes the output device 106 to display a 3D model of at least a portion of the patient's left mandibular arch within the user interface. The user is able to rotate, tumble, pan, zoom in on, zoom out from, or otherwise manipulate the virtual point from which the 3D model of the patient's left mandibular arch is viewed to obtain a desired view of the patient's left mandibular arch. The user then indicates a point on the 3D model of the patient's left mandibular arch corresponding to a peak of the mesiobuccal cusp of the patient's left mandibular first molar (818). Next, the user indicates a point on the 3D model of the patient's left mandibular arch corresponding to a peak of the distobuccal cusp of the patient's left mandibular first molar (820). The user then indicates a point on the 3D model of the patient's left mandibular arch corresponding to a contact point between the patient's left mandibular first molar and the patient's left mandibular second premolar (822). Next, the user indicates a point on the 3D model of the patient's left mandibular arch corresponding to a contact point between the patient's left mandibular first molar and the patient's left mandibular second molar (824). After the user indicates these points on the patient's left mandibular second molar, the occlusion analysis module 122 is able to identify a total occlusion score for the patient. For ease of explanation, the points corresponding to the mesiobuccal cusp of the patient's left mandibular first molar, the distobuccal cusp of the patient's left mandibular first molar, the contact between the patient's left mandibular first molar and the patient's left mandibular second premolar, and the contact between the patient's left mandibular first molar and the patient's left mandibular second molar are referred to herein as the relevant points on the patient's left mandibular first molar.

Subsequently, the user is able to review the results of the occlusion analysis for the patient's left side (826). In various embodiments, the user is able to review the results of the occlusion analysis of the patient's left side in various ways. For example, in some embodiments, the occlusion analysis module 122 causes the output device 106 to display the patient's left side occlusion score and the patient's final occlusion score within the user interface of the case analysis application 102. Furthermore, in some embodiments, the occlusion analysis module 122 causes the output device 106 to display one or more features superimposed on the 3D model of the patient's left mandibular arch. The features indicate to the user how the occlusion analysis module 122 identified the patient's left side occlusion score.

In some embodiments, the occlusion analysis module 122 further assists the user by attempting to automatically identify the true peaks of the mesiobuccal cusps of the patient's maxillary first molars and the relevant points on the patient's mandibular first molars based on user input. For example, the user may indicate a point near the true peak of the mesiobuccal cusp of the patient's right maxillary first molar in step 804. In this example, the occlusion analysis module 122 then attempts to identify a true peak of the mesiobuccal cusp of the patient's right maxillary first molar using the point indicated by the user as a starting place. The occlusion analysis module 122 then automatically adjusts a position of the point to correspond to the identified true peak of the mesiobuccal cusp of the patient's right maxillary first molar. In this way, the occlusion analysis module 122 may be able to help the user more precisely identify the true peak of the mesiobuccal cusp of the patient's right maxillary first molar. Similar examples can be given for the patient's left maxillary first molar and the relevant points on the patient's mandibular first molars. In some embodiments, if the user is not satisfied by the automatically adjusted position of a point, the user is able to override the occlusion analysis module 122 and reposition the point manually.

In some embodiments, the occlusion analysis module 122 automatically attempts to identify the true peak of the mesiobuccal cusp of patient's maxillary first molars and the relevant points on the patient's mandibular first molars prior to receiving input from the user indicating these points. For example, the occlusion analysis module 122 may use a hill climbing algorithm to find each of these points. In such embodiments, the user is able to optionally override the points identified by the occlusion analysis module 122 by manually indicating these points in steps 804-812 and 816-824.

In some instances, the patient may be missing a maxillary first molar, a mandibular first molar, a second mandibular premolar, or a second mandibular molar. When the patient is missing a maxillary first molar, the user can indicate in step 804 an estimated location where the mesiobuccal cusp of the maxillary first molar would be if the patient had the maxillary first molar. Similarly, when the patient is missing a mandibular first molar, the user can indicate in steps 806, 808, 810, and 812 estimated locations where the mesiobuccal cusps and contact points of the mandibular first molar would be if the patient had a mandibular first molar. When the patient is missing a second mandibular premolar or a second mandibular molar, the user can indicate in steps 810 or 812 estimated locations where the patient's second mandibular premolar or second mandibular molar would contact the patient's mandibular first molar if the patient had a second mandibular premolar or a second mandibular molar.

Furthermore, in some embodiments, the core module 110 saves the indicated points to a file for later use. The core module 110 is able to subsequently load the file and cause the points to be displayed on the 3D models of the patient's dental arches. In this way, the user is able to resume work on the occlusion analysis.

Figure 10:
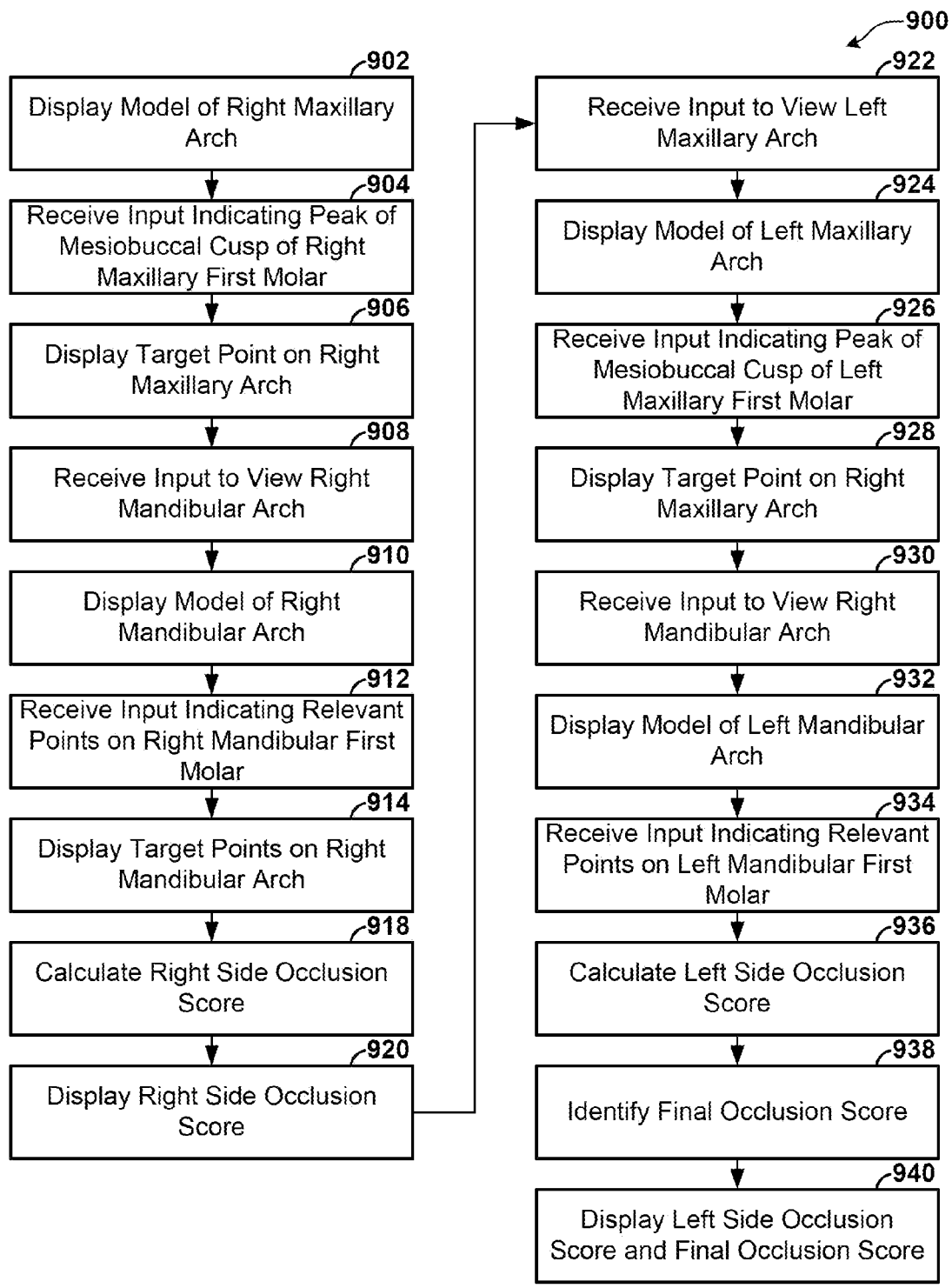
FIG. 10 is a flowchart illustrating an example operation performed by an occlusion analysis module to perform an occlusion analysis.

FIG. 10 is a flowchart illustrating an example operation 900 performed by the occlusion analysis module 122 to perform an occlusion analysis. It should be appreciated that the operation 900 merely represents one example operation to perform an occlusion analysis. In other embodiments, operations to perform an occlusion analysis involve more, fewer, or different steps or include the steps of the operation 900 in different orders.

As illustrated in the example of FIG. 10, the operation 900 begins when the occlusion analysis module 122 causes the output device 106 to display a 3D model of at least a portion of the patient's right maxillary arch within the user interface of the case analysis application 102 (902). In various embodiments, the occlusion analysis module 122 causes the output device 106 to display a 3D model of different portions of the patient's right maxillary arch. For example, in some embodiments, the occlusion analysis module 122 causes the output device 106 to display the patient's entire maxillary arch. In other embodiments, the occlusion analysis module 122 causes the output device 106 to display only the patient's right maxillary first molar. In other embodiments, the occlusion analysis module 122 causes the output device 106 to display the patient's complete right maxillary arch.

While the 3D model of the patient's right maxillary arch is displayed, the occlusion analysis module 122 receives an input indicating a point on the 3D model of the patient's right maxillary arch corresponding to a peak of the mesiobuccal cusp of the patient's right maxillary first molar (904). In response to receiving this input, the occlusion analysis module 122 causes the output device 106 to display a target point on the 3D model of the patient's right maxillary arch at the point corresponding to the peak of the mesiobuccal cusp of the patient's right maxillary first molar (906).

Subsequently, the occlusion analysis module 122 receives an input indicating that the user wants to view a 3D model of the right mandibular arch (908). In response to receiving this input, the occlusion analysis module 122 causes the output device 106 to display the 3D model of at least a portion of the patient's right mandibular arch within the user interface of the case analysis application 102 (910). In various embodiments, the occlusion analysis module 122 causes the output device 106 to display a 3D model of different portions of the patient's right mandibular arch. For example, in some embodiments, the occlusion analysis module 122 causes the output device 106 to display the patient's entire mandibular arch. In other embodiments, the occlusion analysis module 122 causes the output device 106 to display only the patient's right mandibular second premolar, first molar, and second molar. In other embodiments, the occlusion analysis module 122 causes the output device 106 to display the patient's complete right mandibular arch.

While the 3D model of the patient's right mandibular arch is displayed, the occlusion analysis module 122 receives inputs indicating points on the 3D model of the patient's right mandibular arch corresponding to four relevant points on the patient's right mandibular first molar (912). The four relevant points on the right mandibular first molar are the peaks of the buccal cusps of the first molar, a point of contact between the right mandibular first molar and the right mandibular second molar, and a point of contact between the right mandibular first molar and the right mandibular second premolar.

In response to receiving the inputs indicating points corresponding to the four relevant points on the patient's right mandibular first molar, the occlusion analysis module 122 causes the output device 106 to display target points on the 3D model of the patient's right mandibular arch within the user interface of the case analysis application 102 (914). The target points are positioned on the 3D model of the patient's right mandibular arch at the points corresponding to the four relevant points on the patient's right mandibular first molar.

After receiving the inputs indicating the points corresponding to the four relevant points, the occlusion analysis module 122 calculates a right side occlusion score for the patient (918). In various embodiments, the occlusion analysis module 122 calculates the right side occlusion score in various ways. For example, in some embodiments, the occlusion analysis module 122 calculates the right side occlusion score using the operation 1000 illustrated in the example of FIG. 11. After calculating the patient's right side occlusion score, the occlusion analysis module 122 causes the output device 106 to display the right side score within the user interface of the case analysis application 102 (920).

Subsequently, the occlusion analysis module 122 receives input to view a 3D model of at least a portion of the patient's left maxillary arch (922). In response to this input, the occlusion analysis module 122 causes the output device 106 to display the 3D model of at least a portion of the patient's left maxillary arch within the user interface of the case analysis application 102 (924). In various embodiments, the occlusion analysis module 122 causes the output device 106 to display a 3D model of different portions of the patient's left maxillary arch. For example, in some embodiments, the occlusion analysis module 122 causes the output device 106 to display the patient's entire maxillary arch. In other embodiments, the occlusion analysis module 122 causes the output device 106 to display only the patient's left maxillary first molar. In other embodiments, the occlusion analysis module 122 causes the output device 106 to display the patient's complete left maxillary arch.

When the 3D model of the patient's left maxillary arch is displayed, the occlusion analysis module 122 receives input indicating a point on the 3D model of the left maxillary arch corresponding to a peak of the mesiobuccal cusp of the patient's left maxillary first molar (926). In response to receiving this input, the occlusion analysis module 122 causes the output device 106 to display a target point on the 3D model of the patient's left maxillary arch corresponding to the peak of the mesiobuccal cusp of the patient's left maxillary first molar (928).

Next, the occlusion analysis module 122 receives input indicating that the user wants to view a 3D model of at least a portion of the patient's left mandibular arch (930). In response to receiving this input, the occlusion analysis module 122 causes the output device 106 to display a 3D model of at least a portion of the patient's left mandibular arch within the user interface of the case analysis application 102 (932). In various embodiments, the occlusion analysis module 122 causes the output device 106 to display a 3D model of different portions of the patient's left mandibular arch. For example, in some embodiments, the occlusion analysis module 122 causes the output device 106 to display the patient's entire mandibular arch. In other embodiments, the occlusion analysis module 122 causes the output device 106 to display only the patient's right mandibular second premolar, first molar, and second molar. In other embodiments, the occlusion analysis module 122 causes the output device 106 to display the patient's complete right mandibular arch.

When the 3D model of the patient's left mandibular arch is displayed, the occlusion analysis module 122 receives input indicating the relevant points on the patient's left mandibular first molar (934). As discussed above, the four relevant points on the patient's left mandibular first molar are: the peaks of the buccal cusps of the left mandibular first molar, a point of contact between the left mandibular first molar and the left mandibular second molar, and a point of contact between the left mandibular first molar and the left mandibular second premolar.

The occlusion analysis module 122 then calculates a left side occlusion score of the patient (936). In some embodiments, the occlusion analysis module 122 calculates the patient's left side occlusion score in the same way that the occlusion analysis module 122 calculates the right side occlusion score.

After calculating the patient's left side occlusion score, the occlusion analysis module 122 identifies a final occlusion score for the patient (938). In various embodiments, the occlusion analysis module 122 identifies the patient's final occlusion score in various ways. For example, in some embodiments, the occlusion analysis module 122 identifies the patient's final occlusion score as the sum of the patient's left side occlusion score and the patient's right side occlusion score. In other embodiments, the occlusion analysis module 122 identifies the patient's final occlusion score as the greatest of the patient's left side occlusion score and the patient's right side occlusion score.

After identifying the patient's final occlusion score, the occlusion analysis module 122 causes the output device 106 to display the patient's left side occlusion score and the patient's final occlusion score within the user interface of the case analysis application 102 (940).

Figure 11:
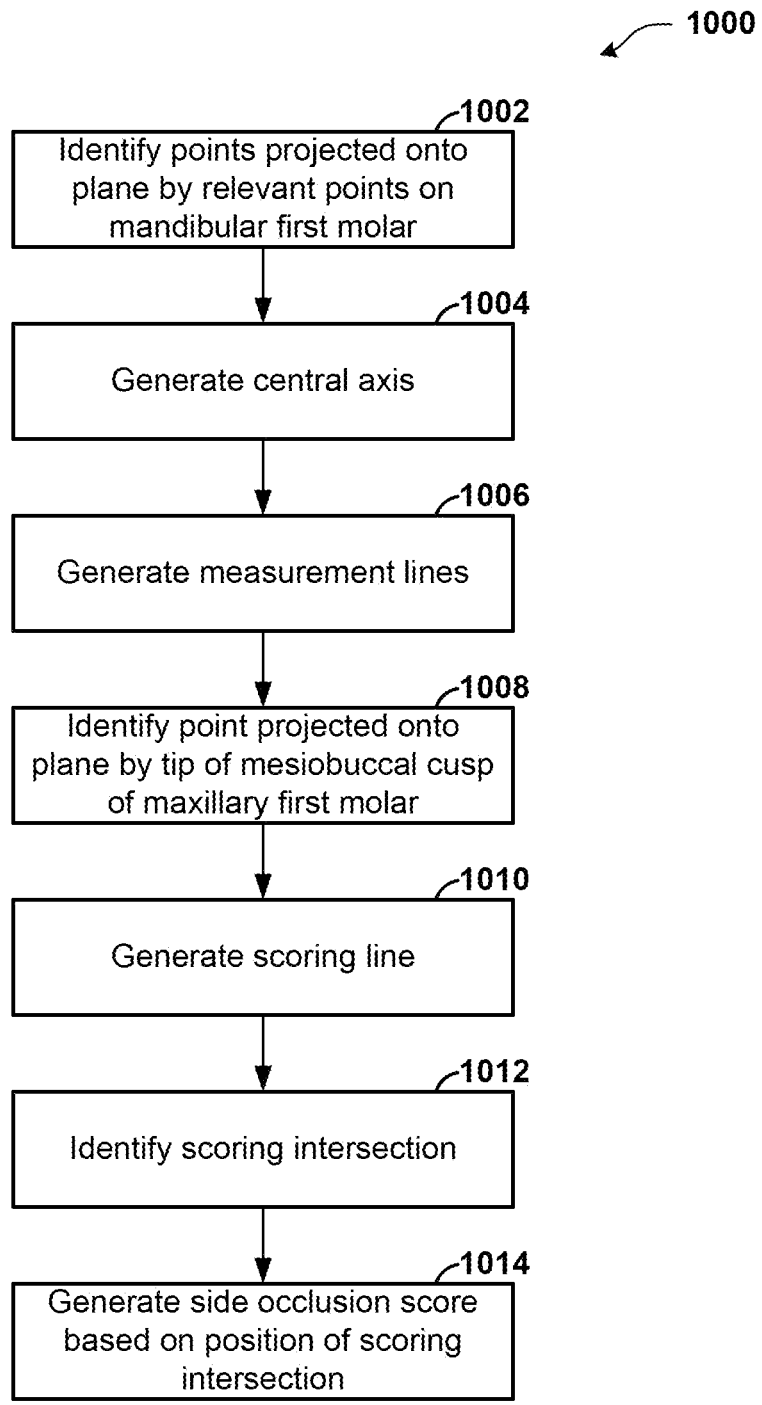
FIG. 11 is a flowchart illustrating an example operation to identify a side occlusion score.

FIG. 11 is a flowchart illustrating an example operation 1000 to identify a side occlusion score. It should be appreciated that the operation 1000 merely represents one example operation to determine a side occlusion score. In other embodiments, operations to determine a side occlusion score involve more, fewer, or different steps or include the steps of the operation 1000 in different orders.

As illustrated in the example of FIG. 11, the occlusion analysis module 122 identifies points projected onto a plane by the relevant points on the patient's mandibular first molar (1002). The plane is parallel to the patient's occlusal plane. As discussed above, the relevant points on the mandibular first molar are the buccal cusps of the mandibular first molar, the point of contact between the first mandibular molar and an adjacent second mandibular molar, and the point of contact between the first mandibular molar and an adjacent second mandibular premolar. For ease of discussion, the points projected onto the plane by the relevant points on the mandibular first molar are referred to herein as the projected relevant points.

Next, the occlusion analysis module 122 generates a central axis (1004). The central axis is a line on the plane. In various embodiments, the occlusion analysis module 122 generates the central axis in various ways. For example, the occlusion analysis module 122 can calculate the central axis as a linear regression over the projected relevant points. In another example, the occlusion analysis module 122 can calculate the central axis as a line through the points projected onto the plane by the buccal cusps of the mandibular first molar. In yet another example, the occlusion analysis module 122 can calculate the central axis as a line through the points projected onto the plane by the points of contact between the first mandibular molar and the adjacent second mandibular molar and the first mandibular molar and the adjacent second mandibular molar.

The occlusion analysis module 122 then generates a set of measurement lines in the plane (1006). Each of the measurement lines is perpendicular to the central axis. The set of measurement lines includes a measurement line through each of the projected relevant points.

The occlusion analysis module 122 then identifies a point projected onto the plane by the point corresponding to the peak of the mesiobuccal cusp of the patient's maxillary first molar (1008). Next, the occlusion analysis module 122 generates a scoring line (1010). The scoring line is a line in the plane. The scoring line is perpendicular to the central axis and passes through the point projected onto the plane by the point corresponding to the peak of the mesiobuccal cusp of the patient's maxillary first molar.

After generating the scoring line, the occlusion analysis module 122 identifies a scoring intersection (1012). The scoring intersection is a point where the scoring line and the central axis intersect. The occlusion analysis module 122 then generates a side occlusion score based on the position of the scoring intersection relative to the positions of measurement intersections (1014). The measurement intersections are points where the central axis and the measurement lines intersect. In various examples, the occlusion analysis module 122 generates the side occlusion score in various ways. For example, scoring zones can exist between the measurement lines. Each of the scoring zones is associated with a score. In this example, the occlusion analysis module 122 can identify the side occlusion score by identifying the scoring zone that contains the scoring intersection and using the score associated with the identified scoring zone as the side score. For instance, the side occlusion score may be "4" when the scoring intersection is less than one millimeter beyond the intersection of the central axis and the measurement line through the contact point between the mandibular first molar and the mandibular second premolar. In various embodiments, the occlusion analysis module 122 assigns various side occlusion scores for the same positions of the scoring line.

In some embodiments, the occlusion analysis module 122 receives additional input from the user. The additional input indicates an adjustment to a given one of the points previous indicated by the user. For example, the additional input may indicate an adjustment to the point corresponding to the mesiobuccal cusp of the patient's right maxillary first molar. In response to receiving the additional input, the occlusion analysis module 122 automatically re-generates the central axis, automatically re-identifies the location of the scoring intersection, and automatically re-generates the side occlusion score. Furthermore, the occlusion analysis module 122 then automatically causes the output device 106 to display an updated final occlusion score based in part on the re-generated side score. In this way, the user may be able to see the effects on the final occlusion score in essentially real time of adjustments to the points.

Figure 12:
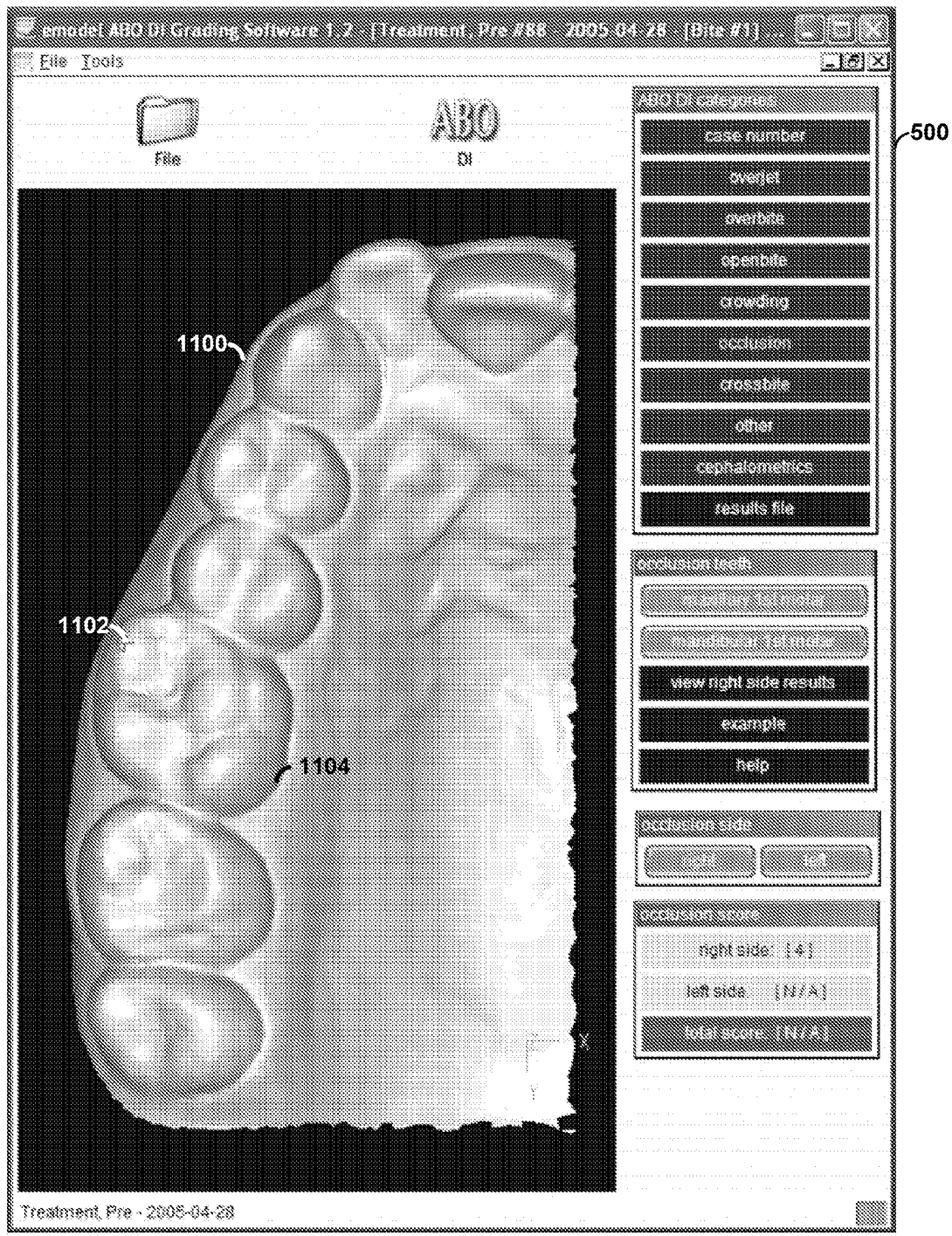
FIG. 12 is an example screen illustration showing the user interface after the user has indicated a point corresponding to a peak of a mesiobuccal cusp of the patient's right maxillary first molar.

FIG. 12 is an example screen illustration showing the user interface 500 after the user has indicated a point corresponding to a peak of a mesiobuccal cusp of a patient's right maxillary first molar. When the user is performing step 804 of the occlusion analysis operation 800 (FIG. 9), the user interface 500 contains a 3D model 1100 of a right maxillary arch. The user selects a point on the 3D model 1100 that corresponds to a peak of a mesiobuccal cusp of the patient's first maxillary molar 1104. In response, the occlusion analysis module 122 causes the output device 106 to display in the user interface 500 a target point 1102 at the point indicated by the user.

Figure 13:
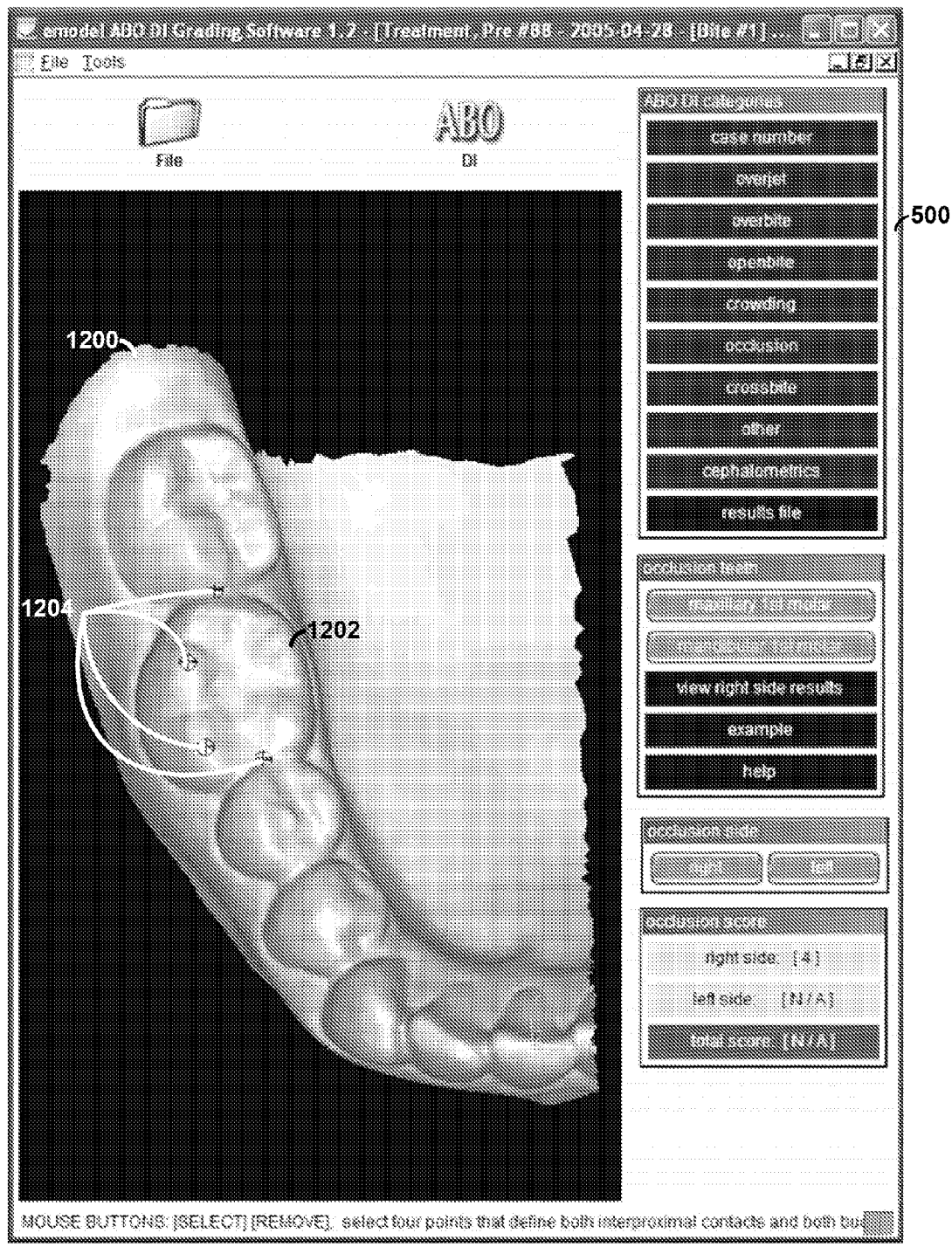
FIG. 13 is an example screen illustration showing the user interface after the user has indicated relevant points on the patient's right mandibular first molar.

FIG. 13 is an example screen illustration showing the user interface 500 after the user has indicated the relevant points on a patient's right mandibular first molar. When the user is performing steps 808-812 of the occlusion analysis operation 800 (FIG. 9), the user interface 500 contains a 3D model 1200 of the patient's right maxillary arch. The user indicates the four relevant points on the patient's right mandibular first molar 1202. In response to the user indicating the relevant points, the occlusion analysis module 122 causes the output device 106 to display target points 1204 at the points indicated by the user.

Figure 14:
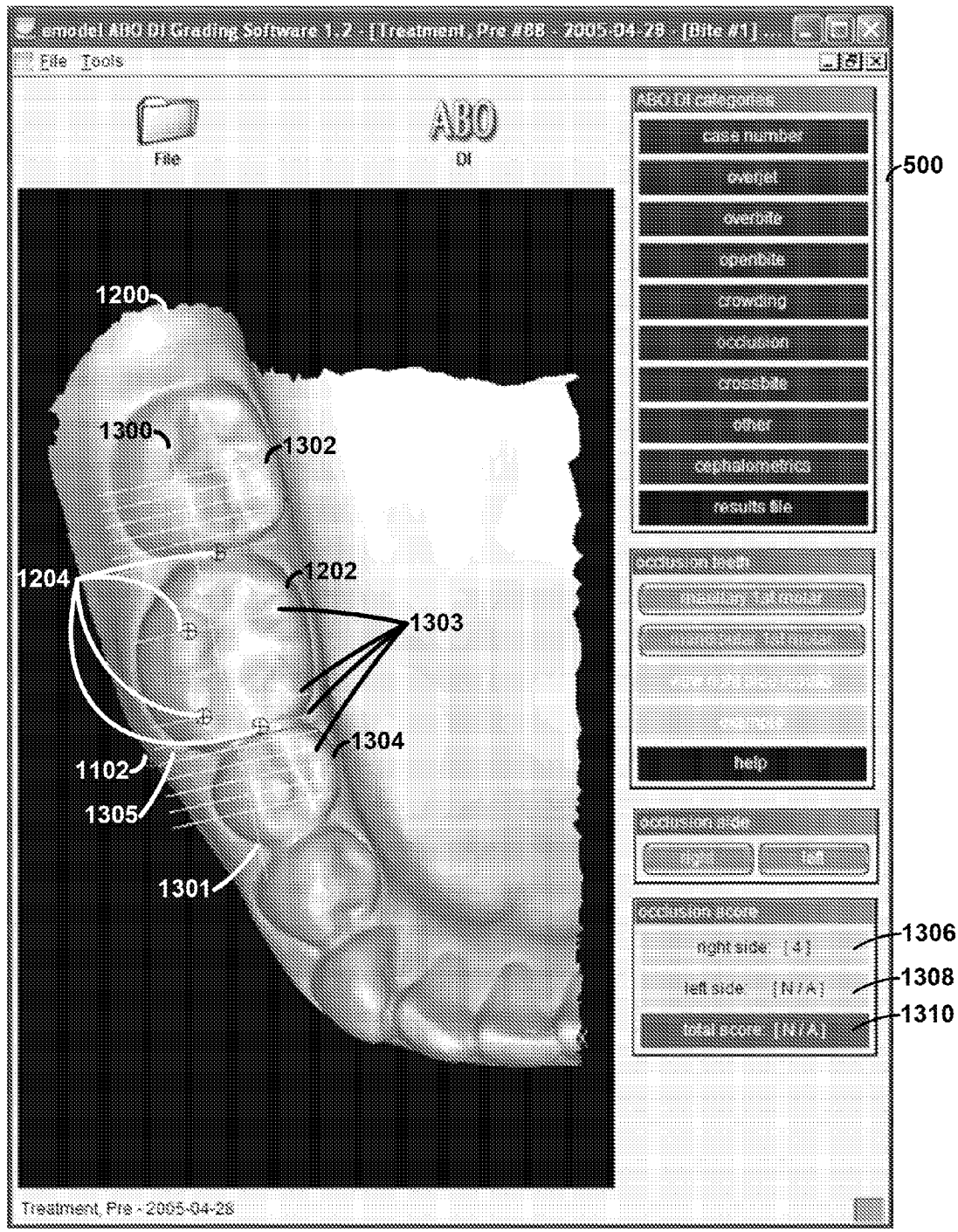
FIG. 14 is an example screen illustration showing the user interface after calculation of an occlusion score for the patient's right side.

FIG. 14 is an example screen illustration showing the user interface 500 after calculation of an occlusion analysis score for the patient's right side. When the user is performing step 814 of the occlusion analysis operation 800 (FIG. 9), the user interface 500 contains the 3D model 1200 of the right maxillary arch. In addition, the user interface 500 contains the target points 1204. Furthermore, the target point 1102 is projected onto the 3D model 1200. As discussed elsewhere, the target point 1102 indicates a peak of a mesiobuccal cusp of the patient's right maxillary first molar 1104.

Ideally, the mesiobuccal cusp of the patient's right maxillary first molar 1104 should be positioned in the area between the buccal cusps of the patient's right mandibular first molar 1202. When the position of the mesiobuccal cusp of the patient's right maxillary first molar 1104 is not in the area between the buccal cusps of the patient's right mandibular first molar 1202, the patient likely has a malocclusion. The malocclusion becomes progressively more severe when the mesiobuccal cusp of the patient's right maxillary first molar 1104 is further from the area between the buccal cusps of the patient's right mandibular first molar 1202.

In the example of FIG. 14, the user interface 500 contains a measurement feature 1300. The measurement feature 1300 includes a central axis 1301 and a set of measurement lines 1303. For clarity in FIG. 14, lines are only shown to some of the measurement lines 1303. Each line in the set of measurement lines 1303 is disposed perpendicular to the central axis 1301. The occlusion analysis module 122 derives the central axis 1301 by linear regression of points projected onto a plane by the four relevant points on the patient's right mandibular first molar 1202. The set of measurement lines 1303 includes a measurement line through each point projected onto the plane by the four relevant points. In addition, the set of measurement lines 1303 includes measurement lines indicating each of the first five millimeters outside the measurement line through the contact point between the patient's right mandibular first molar 1202 and the patient's right mandibular second molar 1302. In addition, the set of measurement lines 1303 includes measurement lines indicating each of the first five millimeters outside the measurement line through the contact point between the patient's right mandibular first molar 1202 and the patient's right mandibular second premolar 1304.

In addition, the measurement feature 1300 includes a scoring line 1305. The scoring line 1305 is perpendicular to the central axis 1301 and passes through the target point 1102. The occlusion score for the patient's right side is calculated based on where the scoring line 1305 intersects the central axis 1301. In the example of FIG. 14, the scoring line 1305 intersects the central axis 1301 between the measurement line through the contact point between the patient's right mandibular first molar 1202 and the patient's right mandibular second premolar 1304 and the measurement line that indicates one millimeter outside the measurement line through the contact point between the patient's right mandibular first molar 1202 and the patient's right mandibular second premolar 1304.

The user interface 500 includes a right side occlusion score feature 1306. The right side occlusion score feature 1306 indicates the patient's right side occlusion score. In the example of FIG. 14, the right side occlusion score feature 1306 indicates that the patient's right side occlusion score is four.

The user interface 500 also includes a left side occlusion score feature 1308 and a total occlusion score feature 1310. The left side occlusion score feature 1308 indicates the patient's left side occlusion score. The final occlusion score feature 1310 indicates the patient's final occlusion score. In example of FIG. 14, an occlusion analysis has not yet been performed on the patient's left side. Consequently, the left side occlusion score feature 1308 indicates no applicable left side occlusion score and the final occlusion score feature 1310 indicates no applicable total occlusion score.

Figure 15:
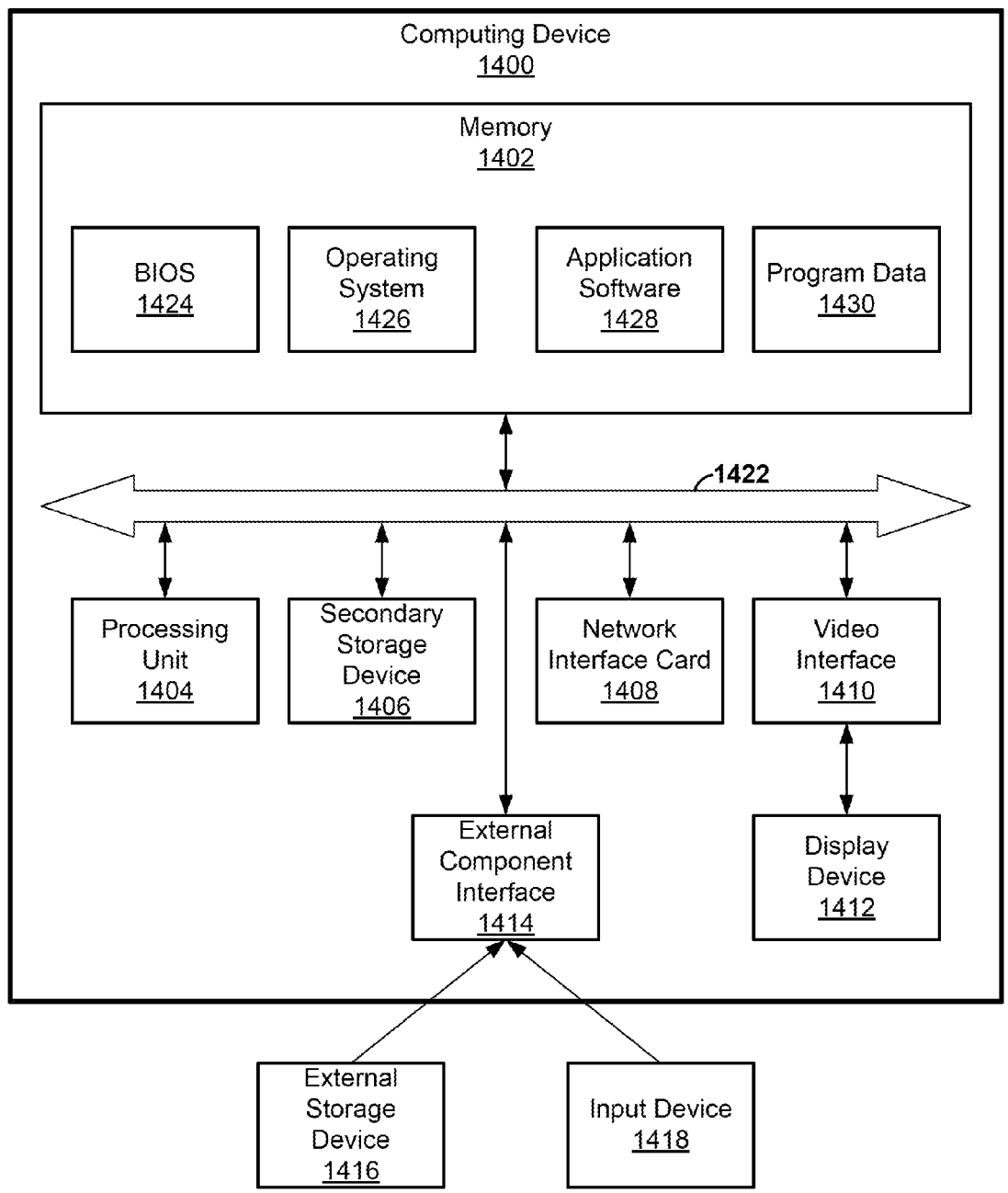
FIG. 15 is a block diagram illustrating example physical components of a computing device.

FIG. 15 is a block diagram illustrating example physical components of a computing device 1400. In some embodiments, the computing system 4 is implemented using physical components of the computing device 1400. It should be appreciated that in other embodiments, the computing system 4 is implemented using physical components other than those illustrated in the example of FIG. 15.

In the example of FIG. 15, the computing device 1400 comprises a memory 1402, a processing unit 1404, a secondary storage device 1406, a network interface card 1408, a video interface 1410, a display device 1412, an external component interface 1414, an external storage device 1416, an input device 1418, and a communication medium 1422. In other embodiments, computing devices are implemented using more or fewer hardware components. For instance, in another example embodiment, a computing device does not include a video interface, a display device, an external storage device, or an input device.

The memory 1402 includes one or more computer-readable data storage media capable of storing data and/or instructions. In different embodiments, the memory 1402 is implemented in different ways. For instance, in various embodiments, the memory 1402 is implemented using various types of computer-readable data storage media. Example types of computer-readable data storage media include, but are not limited to, dynamic random access memory (DRAM), double data rate synchronous dynamic random access memory (DDR SDRAM), reduced latency DRAM, DDR2 SDRAM, DDR3 SDRAM, Rambus RAM, solid state memory, flash memory, read-only memory (ROM), electrically-erasable programmable ROM, and other types of devices and/or articles of manufacture that store data.

The processing unit 1404 includes one or more physical integrated circuits that selectively execute software instructions. In various embodiments, the processing unit 1404 is implemented in various ways. For instance, in one example embodiment, the processing unit 1404 is implemented as one or more processing cores. For instance, in this example embodiment, the processing unit 1404 may be implemented as one or more Intel Core microprocessors. In another example embodiment, the processing unit 1404 is implemented as one or more separate microprocessors. In yet another example embodiment, the processing unit 1404 is implemented as an ASIC that provides specific functionality. In yet another example embodiment, the processing unit 1404 provides specific functionality by using an ASIC and by executing software instructions.

In different embodiments, the processing unit 1404 executes software instructions in different instruction sets. For instance, in various embodiments, the processing unit 1404 executes software instructions in instruction sets such as the x86 instruction set, the POWER instruction set, a RISC instruction set, the SPARC instruction set, the IA-64 instruction set, the MIPS instruction set, and/or other instruction sets.

The secondary storage device 1406 includes one or more computer-readable data storage media. The secondary storage device 1406 stores data and software instructions not directly accessible by the processing unit 1404. In other words, the processing unit 1404 performs an I/O operation to retrieve data and/or software instructions from the secondary storage device 1406. In various embodiments, the secondary storage device 1406 is implemented by various types of computer-readable data storage media. For instance, the secondary storage device 1406 may be implemented by one or more magnetic disks, magnetic tape drives, CD-ROM discs, DVD-ROM discs, Blu-Ray discs, solid state memory devices, Bernoulli cartridges, and/or other types of computer-readable data storage media.

The network interface card 1408 enables the computing device 1400 to send data to and receive data from a computer communication network. In different embodiments, the network interface card 1408 is implemented in different ways. For example, in various embodiments, the network interface card 1408 is implemented as an Ethernet interface, a token-ring network interface, a fiber optic network interface, a wireless network interface (e.g., WiFi, WiMax, etc.), or another type of network interface.

The video interface 1410 enables the computing device 1400 to output video information to the display device 1412. In different embodiments, the video interface 1410 is implemented in different ways. For instance, in one example embodiment, the video interface 1410 is integrated into a motherboard of the computing device 1400. In another example embodiment, the video interface 1410 is a video expansion card. Example types of video expansion cards include Radeon graphics cards manufactured by ATI Technologies, Inc. of Markham, Ontario, Geforce graphics cards manufactured by Nvidia Corporation of Santa Clara, Calif., and other types of graphics cards.

In various embodiments, the display device 1412 is implemented as various types of display devices. Example types of display devices include, but are not limited to, cathode-ray tube displays, LCD display panels, plasma screen display panels, touch-sensitive display panels, LED screens, projectors, and other types of display devices. In various embodiments, the video interface 1410 communicates with the display device 1412 in various ways. For instance, in various embodiments, the video interface 1410 communicates with the display device 1412 via a Universal Serial Bus (USB) connector, a VGA connector, a digital visual interface (DVI) connector, an S-Video connector, a High-Definition Multimedia Interface (HDMI) interface, a DisplayPort connector, or other types of connectors.

The external component interface 1414 enables the computing device 1400 to communicate with external devices. In various embodiments, the external component interface 1414 is implemented in different ways. For instance, in one example embodiment, the external component interface 1414 is a USB interface. In other example embodiments, the computing device 1400 is a FireWire interface, a serial port interface, a parallel port interface, a PS/2 interface, and/or another type of interface that enables the computing device 1400 to communicate with external components.

In different embodiments, the external component interface 1414 enables the computing device 1400 to communicate with different external components. For instance, in the example of FIG. 15, the external component interface 1414 enables the computing device 1400 to communicate with the external storage device 1416, and the input device 1418. In other embodiments, the external component interface 1414 enables the computing device 1400 to communicate with more or fewer external components. Other example types of external components include, but are not limited to, speakers, phone charging jacks, modems, media player docks, other computing devices, scanners, digital cameras, a fingerprint reader, and other devices that can be connected to the computing device 1400.

The external storage device 1416 is an external component comprising one or more computer readable data storage media. Different implementations of the computing device 1400 interface with different types of external storage devices. Example types of external storage devices include, but are not limited to, magnetic tape drives, flash memory modules, magnetic disk drives, optical disc drives, flash memory units, zip disk drives, optical jukeboxes, and other types of devices comprising one or more computer-readable data storage media. The input device 1418 is an external component that provides user input to the computing device 1400. Different implementations of the computing device 1400 interface with different types of input devices. Example types of input devices include, but are not limited to, keyboards, mice, trackballs, stylus input devices, key pads, microphones, joysticks, touch-sensitive display screens, and other types of devices that provide user input to the computing device 1400.

The communications medium 1422 facilitates communication among the hardware components of the computing device 1400. In different embodiments, the communications medium 1422 facilitates communication among different components of the computing device 1400. For instance, in the example of FIG. 15, the communications medium 1422 facilitates communication among the memory 1402, the processing unit 1404, the secondary storage device 1406, the network interface card 1408, the video interface 1410, and the external component interface 1414. In different implementations of the computing device 1400, the communications medium 1422 is implemented in different ways. For instance, in different implementations of the computing device 1400, the communications medium 1422 may be implemented as a PCI bus, a PCI Express bus, an accelerated graphics port (AGP) bus, an Infiniband interconnect, a serial Advanced Technology Attachment (ATA) interconnect, a parallel ATA interconnect, a Fiber Channel interconnect, a USB bus, a Small Computer System Interface (SCSI) interface, or another type of communications medium.

The memory 1402 stores various types of data and/or software instructions. For instance, in the example of FIG. 15, the memory 1402 stores a Basic Input/Output System (BIOS) 1424, an operating system 1426, application software 1428, and program data 1430. The BIOS 1424 includes a set of software instructions that, when executed by the processing unit 1404, cause the computing device 1400 to boot up. The operating system 1426 includes a set of software instructions that, when executed by the processing unit 1404, cause the computing device 1400 to provide an operating system that coordinates the activities and sharing of resources of the computing device 1400. Example types of operating systems include, but are not limited to, Microsoft Windows, Linux, Unix, Apple OS X, Apple OS X iPhone, Palm webOS, Palm OS, Google Chrome OS, Google Android OS, and so on. The application software 1428 includes a set of software instructions that, when executed by the processing unit 1404, cause the computing device 1400 to provide applications to a user of the computing device 1400. The program data 1430 is data generated and/or used by the application software 1428.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

We claim:

1. A computing device comprising:
    a processing unit; and
    a set of computer-readable data storage media comprising at least one computer-readable data storage medium, the set of computer-readable data storage media storing software instructions that, when executed by the processing unit, cause the computing device to:
        for both a right side of a patient and a left side of the patient:
            display a three-dimensional (3D) model of at least a portion of a maxillary arch of the patient;
            receive input indicating a first point on the electronic 3D model of the portion of the maxillary arch, the first point corresponding to a tip of a mesiobuccal cusp of a maxillary first molar;
            display an electronic 3D model of at least a portion of a mandibular arch of the patient;
            receive input indicating a second point on the electronic 3D model of the portion of the mandibular arch, the second point corresponding to a tip of a mesiobuccal cusp of a mandibular first molar;
            receive input indicating a third point on the electronic 3D model of the portion of the mandibular arch, the third point corresponding to a tip of a distobuccal cusp of the mandibular first molar;
            receive input indicating a fourth point on the electronic 3D model of the portion of the mandibular arch, the fourth point corresponding to a contact point between the mandibular first molar and a mandibular second premolar;
            receive input indicating a fifth point on the electronic 3D model of the portion of the mandibular arch, the fifth point corresponding to a contact point between the mandibular first molar and a mandibular second molar;
            generate a central axis by calculating a linear regression of points projected onto a plane by the second point, the third point, the fourth point, and the fifth point, the central axis being a line on the plane, the plane being parallel to an occlusal plane of the patient;
            identify a location of a scoring intersection, the scoring intersection being a point where the central axis and a scoring line intersect, the scoring line being a line on the plane, the scoring line being perpendicular to the central axis and passing through a point projected onto the plane by the first point; and
            generate a side score based on the location of the scoring intersection relative to measurement intersections, the measurement intersections being points where the central axis and measurement lines intersect, the measurement lines being lines on the plane, the measurement lines including lines perpendicular to the central axis and passing through the points projected onto the plane by the second point, the third point, the fourth point, and the fifth point; and
        display a final occlusion score for the patient, the final occlusion score based on the side score for the right side and the side score for the left side.

2. The computing device of claim 1, wherein the software instructions, when executed by the processing unit, further cause the computing device to:
    in response to receiving the input indicating the first point:
        attempt to identify a true tip of the mesiobuccal cusp of the maxillary first molar; and
        adjust a position of the first point to correspond to the true tip of the mesiobuccal cusp of the maxillary first molar;
    in response to receiving the input indicating the second point:
        attempt to identify a true tip of the mesiobuccal cusp of the mandibular first molar; and
        adjust a position of the second point to correspond to the true tip of the mesiobuccal cusp of the mandibular first molar; and
    in response to receiving the input indicating the third point:
        attempt to identify a true tip of the distobuccal cusp of the mandibular first molar; and
        adjust a position of the third point to correspond to the true tip of the distobuccal cusp of the mandibular first molar.

3. The computing device of claim 1, wherein the software instructions, when executed by the processing unit, further cause the computing device to:
    attempt, prior to receiving the input indicating the first point, to identify a true tip of the mesiobuccal cusp of the maxillary first molar;
    attempt, prior to receiving the input indicating the second point, to identify a true tip of the mesiobuccal cusp of the mandibular first molar; and
    attempt, prior to receiving the input indicating the third point, to identify a true tip of the distobuccal cusp of the mandibular first molar.

4. The computing device of claim 1, wherein the software instructions, when executed by the processing unit, further cause the computing device to:
    display, in response to receiving the input indicating the first point, the first point on the electronic 3D model of the portion of the maxillary arch;
    display, in response to receiving the input indicating the second point, the second point on the electronic 3D model of the portion of the mandibular arch;
    display, in response to receiving the input indicating the third point, the third point on the electronic 3D model of the portion of the mandibular arch.

5. The computing device of claim 1, wherein the software instructions, when executed by the processing unit, further cause the computing device to: display, on the electronic 3D model of the portion of the mandibular arch, the central axis, the measurement lines, the scoring line, the point projected onto the plane by the first point, the point projected onto the plane by the second point, the point projected onto the plane by the third point, the point projected onto the plane by the fourth point, and the point projected onto the plane by the fifth point.

6. The computing device of claim 5, wherein the measurement lines further include:
    lines perpendicular to the central axis and representing distances beyond the measurement line passing through the point projected onto the plane by the fourth point; and lines perpendicular to the central axis and representing distances beyond the measurement line passing through the point projected onto the plane by the fifth point.

7. The computing device of claim 6, wherein the software instructions, when executed by the processing unit, cause the computing device to calculate the final occlusion score by adding the side score for the right side and the side score for the left side.

8. A computer-readable data storage medium comprising software instructions that, when executed by a processing unit of a computing device, cause the computing device to:
for both a right side of a patient and a left side of the patient:
display a three-dimensional (3D) model of at least a portion of a maxillary arch of the patient;
receive input indicating a first point on the electronic 3D model of the portion of the maxillary arch, the first point corresponding to a tip of a mesiobuccal cusp of a first maxillary molar;
display an electronic 3D model of at least a portion of a mandibular arch of the patient;
receive input indicating a second point on the electronic 3D model of the portion of the mandibular arch, the second point corresponding to a tip of a mesiobuccal cusp of a first mandibular molar;
receive input indicating a third point on the electronic 3D model of the portion of the mandibular arch, the third point corresponding to a tip of a distobuccal cusp of the first mandibular molar;
receive input indicating a fourth point on the electronic 3D model of the portion of the mandibular arch, the fourth point corresponding to a contact point between the first mandibular molar and a second mandibular premolar;
receive input indicating a fifth point on the electronic 3D model of the portion of the mandibular arch, the fifth point corresponding to a contact point between the first mandibular molar and a second mandibular molar;
generate a central axis by calculating a linear regression of points projected onto a plane by the second point, the third point, the fourth point, and the fifth point, the central axis being a line on the plane, the plane being parallel to an occlusal plane of the patient;
identify a location of a scoring intersection, the scoring intersection being a point where the central axis and a scoring line intersect, the scoring line being a line on the plane, the scoring line being perpendicular to the central axis and passing through a point projected onto the plane by the first point; and
generate a side score based on the location of the scoring intersection relative to measurement intersections, the measurement intersections being points where the central axis and measurement lines intersect, the measurement lines being lines on the plane, the measurement lines including lines perpendicular to the central axis and passing through the points projected onto the plane by the second point, the third point, the fourth point, and the fifth point; and
display a final occlusion score for the patient, the final occlusion score based on the side score for the right side and the side score for the left side.

9. A method for analyzing occlusion, the method comprising:
providing, to a computing device, input indicating a first point on an electronic 3D model of a portion of a maxillary arch of a patient, the first point corresponding to a tip of a mesiobuccal cusp of a first maxillary molar;
providing, to the computing device, input indicating a second point on an electronic 3D model of the portion of a mandibular arch of the patient, the second point corresponding to a tip of a mesiobuccal cusp of a first mandibular molar;
providing, to the computing device, input indicating a third point on the electronic 3D model of the portion of the mandibular arch, the third point corresponding to a tip of a distobuccal cusp of the first mandibular molar;
providing, to the computing device, input indicating a fourth point on the electronic 3D model of the portion of the mandibular arch, the fourth point corresponding to a contact point between the first mandibular molar and a second mandibular premolar; and
providing, to the computing device, input indicating a fifth point on the electronic 3D model of the portion of the mandibular arch, the fifth point corresponding to a contact point between the first mandibular molar and a second mandibular molar;
reviewing, by a user, a final occlusion score for the patient, the final occlusion score being based at least in part on a side score of the patient,
wherein the side score of the patient is based on a location of a scoring intersection relative to measurement intersections,
wherein the measurement intersections are points where a central axis and measurement lines intersect,
wherein the measurement lines are lines on a plane,
wherein the plane is parallel to an occlusal plane of the patient,
wherein the measurement lines include lines that are perpendicular to the central axis and that pass through points projected onto the plane by the second point, the third point, the fourth point, and the fifth point,
wherein the central axis is a linear regression of the points projected onto the plane by the second point, the third point, the fourth point, and the fifth point, the central axis being a line on the plane,
wherein the scoring intersection is a point where the central axis and a scoring line intersect,
wherein the scoring line is a line on the plane, and
wherein the scoring line is perpendicular to the central axis and passes through the point projected onto the plane by the first point.

* * * * *